(12) United States Patent
Kramer

(10) Patent No.: US 7,514,122 B2
(45) Date of Patent: *__Apr. 7, 2009__

(54) METHOD AND APPARATUS FOR SPRAY PROCESSING OF POROUS MEDICAL DEVICES

(75) Inventor: Pamela A. Kramer, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 100 days.

This patent is subject to a terminal disclaimer.

(21) Appl. No.: 11/582,703

(22) Filed: Oct. 17, 2006

(65) Prior Publication Data

US 2007/0036905 A1    Feb. 15, 2007

Related U.S. Application Data

(60) Division of application No. 10/331,838, filed on Dec. 30, 2002, now Pat. No. 7,163,715, which is a continuation-in-part of application No. 09/880,514, filed on Jun. 12, 2001, now Pat. No. 7,201,940.

(51) Int. Cl.
*B05D 1/02* (2006.01)
*B05D 1/08* (2006.01)
*B05D 7/00* (2006.01)
*B29B 15/10* (2006.01)
*C23C 4/02* (2006.01)
*B29D 22/00* (2006.01)
*B22F 3/115* (2006.01)
*B22F 5/12* (2006.01)
*A61F 2/06* (2006.01)

(52) U.S. Cl. ............ 427/421.1; 427/446; 427/447; 427/448; 427/455; 427/189; 427/427.1; 428/34.1; 428/36.5; 428/547; 428/586; 428/587; 623/1.15; 623/1.39

(58) Field of Classification Search ............ 428/547, 428/586–587, 34.1, 36.5; 427/421.1, 427.1, 427/189, 191
See application file for complete search history.

(56) References Cited

U.S. PATENT DOCUMENTS 3,105,492 A    10/1963    Jeckel
(Continued)

FOREIGN PATENT DOCUMENTS

CA    2008312    7/1990
(Continued)

OTHER PUBLICATIONS

Vardelle, A., et al.; "The Dynamics of Deposit Formation in Thermal-Spray Processes," *MRS Bulletin*, Jul. 2000, pp. 32-37.
(Continued)

*Primary Examiner*—William Phillip Fletcher, III
*Assistant Examiner*—Cachet I Sellman
(74) *Attorney, Agent, or Firm*—Squire, Sanders & Dempsey L.L.P.

(57) ABSTRACT

Thermal spray processing and cold spray processing are utilized to manufacture porous starting materials (such as tube stock, wire and substrate sheets) from biocompatible metals, metal alloys, ceramics and polymers that may be further processed into porous medical devices, such as stents. The spray processes are also used to form porous coatings on consolidated biocompatible medical devices. The porous substrates and coatings may be used as a reservoir to hold a drug or therapeutic agent for elution in the body. The spray-formed porous substrates and coatings may be functionally graded to allow direct control of drug elution without an additional polymer topcoat. The spray processes are also used to apply the drug or agent to the porous substrate or coating when drug or agent is robust enough to withstand the temperatures and velocities of the spray process with minimal degradation.

24 Claims, 11 Drawing Sheets

U.S. PATENT DOCUMENTS

| | | |
|---|---|---|
| 3,288,728 A | 11/1966 | Gorham |
| 3,657,744 A | 4/1972 | Ersek |
| 3,839,743 A | 10/1974 | Schwarcz |
| 3,993,078 A | 11/1976 | Bergentz et al. |
| 4,130,904 A | 12/1978 | Whalen |
| 4,140,126 A | 2/1979 | Choudhury |
| 4,159,719 A | 7/1979 | Haar |
| 4,346,028 A | 8/1982 | Griffith |
| 4,411,055 A | 10/1983 | Simpson et al. |
| 4,503,569 A | 3/1985 | Dotter |
| 4,512,338 A | 4/1985 | Balko et al. |
| 4,531,933 A | 7/1985 | Norton et al. |
| 4,553,545 A | 11/1985 | Maass et al. |
| 4,580,568 A | 4/1986 | Gianturco |
| 4,604,762 A | 8/1986 | Robinson |
| 4,619,246 A | 10/1986 | Molgaard-Nielsen et al. |
| 4,633,873 A | 1/1987 | DumiCanadan et al. |
| 4,649,922 A | 3/1987 | Wiktor |
| 4,650,466 A | 3/1987 | Luther |
| 4,655,771 A | 4/1987 | Wallsten |
| 4,656,083 A | 4/1987 | Hoffman et al. |
| 4,681,110 A | 7/1987 | Wiktor |
| 4,681,734 A | 7/1987 | Simm et al. |
| 4,699,611 A | 10/1987 | Bowden |
| 4,706,671 A | 11/1987 | Weinrib |
| 4,718,907 A | 1/1988 | Karwoski et al. |
| 4,722,335 A | 2/1988 | Vilasi |
| 4,723,549 A | 2/1988 | Wholey et al. |
| 4,728,328 A | 3/1988 | Hughes et al. |
| 4,739,762 A | 4/1988 | Palmaz |
| 4,740,207 A | 4/1988 | Kreamer |
| 4,762,128 A | 8/1988 | Rosenbluth |
| 4,776,337 A | 10/1988 | Palmaz |
| 4,776,337 A | 10/1988 | Palmaz |
| 4,800,882 A | 1/1989 | Gianturco |
| 4,816,339 A | 3/1989 | Tu et al. |
| 4,848,343 A | 7/1989 | Wallstén et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,922,905 A | 5/1990 | Strecker |
| 4,943,346 A | 7/1990 | Mattelin |
| 4,950,227 A | 8/1990 | Savis et al. |
| 4,969,458 A | 11/1990 | Wiktor |
| 4,969,890 A | 11/1990 | Sugita et al. |
| 4,981,478 A | 1/1991 | Evard et al. |
| 4,986,831 A | 1/1991 | King et al. |
| 4,990,155 A | 2/1991 | Wilkoff |
| 4,994,071 A | 2/1991 | MacGregor |
| 4,994,298 A | 2/1991 | Yasuda |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,026,377 A | 6/1991 | Burton et al. |
| 5,034,001 A | 7/1991 | Garrison et al. |
| 5,035,706 A | 7/1991 | Gianturco et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,047,050 A | 9/1991 | Arpesani |
| 5,053,048 A | 10/1991 | Pinchuk |
| 5,059,211 A | 10/1991 | Stack et al. |
| 5,061,275 A | 10/1991 | Wallstén et al. |
| 5,062,829 A | 11/1991 | Pryor et al. |
| 5,064,435 A | 11/1991 | Porter |
| 5,071,407 A | 12/1991 | Termin et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,085,629 A | 2/1992 | Goldberg et al. |
| 5,089,005 A | 2/1992 | Harada |
| 5,092,877 A | 3/1992 | Pinchuk |
| 5,100,429 A | 3/1992 | Sinofsky et al. |
| 5,102,417 A | 4/1992 | Palmaz |
| 5,107,852 A | 4/1992 | Davidson et al. |
| 5,108,416 A | 4/1992 | Ryan et al. |
| 5,108,417 A | 4/1992 | Sawyer |
| 5,108,755 A | 4/1992 | Daniels et al. |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,516 A | 8/1992 | Sahatjian et al. |
| 5,135,536 A | 8/1992 | Hillstead |
| 5,151,105 A | 9/1992 | Kwan-Gett |
| 5,156,623 A | 10/1992 | Hakamatsuka et al. |
| 5,161,547 A | 11/1992 | Tower |
| 5,163,958 A | 11/1992 | Pinchuk |
| 5,171,262 A | 12/1992 | MacGregor |
| 5,176,661 A | 1/1993 | Evard et al. |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,197,977 A | 3/1993 | Hoffman, Jr. et al. |
| 5,206,341 A | 4/1993 | Ibay et al. |
| 5,222,971 A | 6/1993 | Willard et al. |
| 5,226,913 A | 7/1993 | Pinchuk |
| 5,234,416 A | 8/1993 | MaCaulay et al. |
| 5,234,456 A | 8/1993 | Silvestrini |
| 5,234,457 A | 8/1993 | Andersen |
| 5,236,447 A | 8/1993 | Kubo et al. |
| 5,269,802 A | 12/1993 | Garber |
| 5,279,594 A | 1/1994 | Jackson |
| 5,282,823 A | 2/1994 | Schwartz et al. |
| 5,282,860 A | 2/1994 | Matsuno et al. |
| 5,289,831 A | 3/1994 | Bosley |
| 5,290,230 A | 3/1994 | Ainsworth et al. |
| 5,290,271 A | 3/1994 | Jernberg |
| 5,302,414 A * | 4/1994 | Alkhimov et al. ............ 427/192 |
| 5,304,200 A | 4/1994 | Spaulding |
| 5,306,286 A | 4/1994 | Stack et al. |
| 5,314,444 A | 5/1994 | Gianturco |
| 5,314,472 A | 5/1994 | Fontaine |
| 5,330,500 A | 7/1994 | Song |
| 5,342,348 A | 8/1994 | Kaplan |
| 5,342,621 A | 8/1994 | Eury |
| 5,356,433 A | 10/1994 | Rowland et al. |
| 5,358,533 A | 10/1994 | Noiles et al. |
| 5,360,443 A | 11/1994 | Barone et al. |
| 5,364,354 A | 11/1994 | Walker et al. |
| 5,366,504 A | 11/1994 | Andersen et al. |
| 5,370,684 A | 12/1994 | Vallana et al. |
| 5,383,927 A | 1/1995 | De Goicoechea et al. |
| 5,389,106 A | 2/1995 | Tower |
| 5,415,546 A | 5/1995 | Cox, Sr. |
| 5,421,955 A | 6/1995 | Lau et al. |
| 5,423,849 A | 6/1995 | Engelson et al. |
| 5,423,885 A | 6/1995 | Williams |
| 5,449,373 A | 9/1995 | Pinchasik et al. |
| 5,451,209 A | 9/1995 | Ainsworth et al. |

| | | |
|---|---|---|
| 5,464,650 A | 11/1995 | Berg et al. |
| 5,505,984 A * | 4/1996 | England et al. ............ 427/2.24 |
| 5,531,715 A | 7/1996 | Engelson et al. |
| 5,538,512 A | 7/1996 | Zenzon et al. |
| 5,562,621 A | 10/1996 | Claude et al. |
| 5,562,728 A | 10/1996 | Lazarus et al. |
| 5,569,295 A | 10/1996 | Lam |
| 5,571,166 A | 11/1996 | Dinh et al. |
| 5,601,538 A | 2/1997 | Deem |
| 5,601,593 A | 2/1997 | Freitag |
| 5,603,991 A | 2/1997 | Kupiecki et al. |
| 5,607,442 A | 3/1997 | Fischell et al. |
| 5,609,629 A | 3/1997 | Fearnot et al. |
| 5,618,298 A | 4/1997 | Simon |
| 5,624,411 A | 4/1997 | Tuch |
| 5,628,755 A | 5/1997 | Heller et al. |
| 5,628,781 A | 5/1997 | Williams et al. |
| 5,630,829 A | 5/1997 | Lauterjung |
| 5,636,641 A | 6/1997 | Fariabi |
| 5,637,113 A | 6/1997 | Tartaglia et al. |
| 5,639,278 A | 6/1997 | Dereume et al. |
| 5,649,977 A | 7/1997 | Campbell |
| 5,674,241 A | 10/1997 | Bley et al. |
| 5,688,516 A | 11/1997 | Raad et al. |
| 5,690,670 A * | 11/1997 | Davidson .................... 606/198 |
| 5,697,967 A | 12/1997 | Dinh et al. |
| 5,700,286 A | 12/1997 | Tartaglia et al. |
| 5,702,682 A | 12/1997 | Thompson |
| 5,421,955 A | 1/1998 | Lau et al. |
| 5,707,388 A | 1/1998 | Lauterjung |
| 5,713,949 A | 2/1998 | Jayaraman |
| 5,716,406 A | 2/1998 | Farber |
| 5,718,723 A | 2/1998 | Matsuda et al. |
| 5,718,726 A | 2/1998 | Amon et al. |
| 5,725,672 A | 3/1998 | Schmitt et al. |
| 5,730,733 A | 3/1998 | Mortier et al. |
| 5,735,892 A | 4/1998 | Myers et al. |
| 5,741,327 A | 4/1998 | Frantzen |
| 5,749,880 A | 5/1998 | Banas et al. |
| 5,750,206 A | 5/1998 | Hergenrother et al. |
| 5,759,192 A | 6/1998 | Saunders |
| 5,762,625 A | 6/1998 | Igaki |
| 5,766,710 A | 6/1998 | Tumlund et al. |
| 5,769,884 A | 6/1998 | Solovay |
| 5,776,161 A | 7/1998 | Globerman |
| 5,780,807 A | 7/1998 | Saunders |
| 5,788,626 A | 8/1998 | Thompson |
| 5,789,018 A | 8/1998 | Engelson et al. |
| 5,795,626 A | 8/1998 | Gabel et al. |
| 5,800,507 A | 9/1998 | Schwartz |
| 5,810,868 A | 9/1998 | Lashinski et al. |
| 5,810,870 A | 9/1998 | Myers et al. |
| 5,824,046 A | 10/1998 | Smith et al. |
| 5,824,048 A | 10/1998 | Tuch |
| 5,824,049 A * | 10/1998 | Ragheb et al. ............ 623/1.44 |
| 5,824,057 A | 10/1998 | Plaiá et al. |
| 5,833,651 A | 11/1998 | Donovan et al. |
| 5,836,966 A | 11/1998 | St. Germain |
| 5,837,316 A | 11/1998 | Fuchita |
| 5,843,118 A | 12/1998 | Sepoetka et al. |
| 5,843,120 A | 12/1998 | Israel et al. |
| 5,843,164 A | 12/1998 | Frantzen et al. |
| 5,843,171 A | 12/1998 | Campbell et al. |
| 5,868,783 A | 2/1999 | Tower |
| 5,869,127 A | 2/1999 | Zhong |
| 5,902,290 A | 5/1999 | Peacock, III et al. |
| 5,913,895 A | 6/1999 | Burpee et al. |
| 5,928,279 A | 7/1999 | Shannon et al. |
| 5,951,513 A | 9/1999 | Miraki |
| 5,961,545 A | 10/1999 | Lentz et al. |
| 5,961,546 A | 10/1999 | Robinson et al. |
| 5,964,730 A | 10/1999 | Williams et al. |
| 5,968,070 A | 10/1999 | Bley et al. |
| 5,976,179 A | 11/1999 | Inoue |
| 5,980,565 A | 11/1999 | Jayaraman |
| 5,980,566 A | 11/1999 | Alt et al. |
| 5,993,489 A | 11/1999 | Lewis et al. |
| 6,004,310 A | 12/1999 | Bardsley et al. |
| 6,010,521 A | 1/2000 | Lee et al. |
| 6,010,529 A | 1/2000 | Herweck et al. |
| 6,010,530 A | 1/2000 | Goicoechea |
| 6,013,100 A | 1/2000 | Inoue |
| 6,015,429 A | 1/2000 | Lau et al. |
| 6,015,430 A | 1/2000 | Wall |
| 6,019,789 A | 2/2000 | Dinh et al. |
| 6,025,034 A | 2/2000 | Strutt et al. |
| 6,027,526 A | 2/2000 | Limon et al. |
| 6,042,597 A | 3/2000 | Kveen et al. |
| 6,059,770 A | 5/2000 | Peacock, III et al. |
| 6,074,135 A | 6/2000 | Tapphorn et al. |
| 6,090,134 A | 7/2000 | Tu et al. |
| 6,099,559 A | 8/2000 | Nolting |
| 6,099,561 A | 8/2000 | Alt |
| 6,120,536 A | 9/2000 | Ding et al. |
| 6,139,573 A | 10/2000 | Sogard et al. |
| 6,143,022 A | 11/2000 | Shull et al. |
| 6,143,370 A | 11/2000 | Panagiotou et al. |
| 6,156,064 A | 12/2000 | Chouinard |
| 6,159,239 A | 12/2000 | Greenhalgh |
| 6,162,244 A | 12/2000 | Braun et al. |
| 6,165,211 A | 12/2000 | Thompson |
| 6,168,619 B1 | 1/2001 | Dinh et al. |
| 6,174,330 B1 | 1/2001 | Stinson |
| 6,184,266 B1 | 2/2001 | Ronan et al. |
| 6,241,691 B1 | 6/2001 | Ferrera et al. |
| 6,251,136 B1 | 6/2001 | Guruwaiya et al. |
| 6,368,658 B1 | 4/2002 | Schwarz et al. |
| 6,428,579 B1 * | 8/2002 | Valentini ................. 623/23.76 |
| 6,432,133 B1 | 8/2002 | Lau et al. |
| 6,447,848 B1 | 9/2002 | Chow et al. |
| 6,774,278 B1 | 8/2004 | Ragheb et al. |
| 7,163,715 B1 * | 1/2007 | Kramer ...................... 427/189 |
| 2002/0032477 A1 | 3/2002 | Helmus et al. |
| 2002/0042645 A1 | 4/2002 | Shannon |
| 2002/0138136 A1 | 9/2002 | Chandresekaran et al. |

FOREIGN PATENT DOCUMENTS

| | | |
|---|---|---|
| CA | 2007648 | 4/1991 |
| CA | 1322628 | 10/1993 |
| CA | 1336319 | 7/1995 |
| CA | 1338303 | 5/1996 |
| EP | 0 045 627 A1 | 2/1982 |
| EP | 0 201 466 A2 | 11/1986 |
| EP | 0 221 570 A2 | 5/1987 |
| EP | 0 335 341 B1 | 10/1989 |
| EP | 0 338 816 A2 | 10/1989 |
| EP | 0 351 314 B1 | 1/1990 |
| EP | 0 357 003 A2 | 3/1990 |
| EP | 0 364 781 A1 | 4/1990 |
| EP | 0 372 789 A3 | 6/1990 |
| EP | 0 380 668 B1 | 8/1990 |
| EP | 0 407 951 A2 | 1/1991 |
| EP | 0 421 729 A2 | 4/1991 |
| EP | 0 423 916 A1 | 4/1991 |
| EP | 0 517 075 B1 | 12/1992 |
| EP | 0 540 290 A2 | 5/1993 |
| EP | 0 540 290 B1 | 5/1993 |
| EP | 0 565 251 | 10/1993 |
| EP | 0 604 022 A1 | 6/1994 |
| EP | 0 606 165 A1 | 7/1994 |
| EP | 0 621 017 A1 | 10/1994 |
| EP | 0 649 637 A1 | 4/1995 |
| EP | 0 701 802 A1 | 3/1996 |
| EP | 0 716 836 A1 | 6/1996 |
| EP | 0 756 853 A1 | 2/1997 |

| | | |
|---|---|---|
| EP | 0 800 801 A1 | 10/1997 |
| EP | 0 806 190 A1 | 11/1997 |
| EP | 0 824 900 A2 | 2/1998 |
| EP | 0 832 618 A1 | 4/1998 |
| EP | 0 916 317 A1 | 5/1999 |
| EP | 0 938 879 A2 | 9/1999 |
| GB | 2 070 490 A | 9/1981 |
| GB | 2 135 585 A | 4/1982 |
| JP | 49-48336 | 12/1974 |
| JP | 54-18317 | 7/1979 |
| JP | 58-501458 | 9/1983 |
| JP | 60-28504 | 7/1985 |
| JP | 62235496 A | 10/1987 |
| JP | 63-214264 | 9/1988 |
| JP | 62-242292 | 3/1989 |
| JP | 02-174859 | 7/1990 |
| JP | 02-255157 | 10/1990 |
| JP | 03009746 A | 1/1991 |
| JP | 04-25755 | 2/1992 |
| JP | 18-33718 | 2/1996 |
| JP | 10151190 A | 6/1998 |
| WO | WO 91/07139 | 5/1991 |
| WO | WO 91/17789 | 11/1991 |
| WO | WO 92/06734 | 4/1992 |
| WO | WO 92/09246 | 6/1992 |
| WO | WO 93/06792 | 4/1993 |
| WO | WO 94/17754 | 8/1994 |
| WO | WO 95/11817 | 5/1995 |
| WO | WO 95/23563 | 9/1995 |
| WO | WO 95/26695 | 10/1995 |
| WO | WO 96/00103 | 1/1996 |
| WO | WO 96/09013 | 3/1996 |
| WO | WO 96/28115 | 9/1996 |
| WO | WO 97/10011 | 3/1997 |
| WO | WO 97/25937 | 7/1997 |
| WO | WO 98/20927 | 5/1998 |
| WO | WO 98/22159 | 5/1998 |
| WO | WO 98/32412 | 7/1998 |
| WO | WO 98/58600 | 12/1998 |
| WO | WO 98/17680 | 4/1999 |
| WO | WO 99/39661 | 8/1999 |

OTHER PUBLICATIONS

Gitzhofer, F. et al.; "Integrated Fabrication Processes for Solid-Oxide Fuel Cells Using Thermal Plasma Spray Technology," *MRS Bulletin*, Jul. 2000, pp. 38-42.

Zhu, D. et al.; "Thermal-Barrier Coatings for Advanced Gas-Turbine Engines," *MRS Bulletin*, Jul. 2000, pp. 43-47.

Brogan, J. A.; "Thermal-Spraying of Polymers and Polymer Blends," *MRS Bulletin*, Jul. 2000, pp. 48-53.

Web site: http://doL1.eng.sunysb.edu/Berndt/Berndt-NP14/html; "Thermal Spray as a Means to Achieve Nano-Phased Structures," Nov. 27, 2000, 30 pages.

Web site: http//homepage.dtn.ntl.com/gordon.england/tsc.html; "Nature of Thermal Spray Coatings," Nov. 29, 2000, 9 pages.

Wan, Y. P. et al.; "Modeling and Visualization of Plasma Spraying of Functionally Graded Materials and Its Application to the Optimization of Spray Conditions," *Journal of Thermal Spray Technology*, vol. 10(2), Jun. 2001, pp. 382-389.

"Selected Abstracts of Thermal Spray Literature," *Journal of Thermal Spray Technology*, vol. 10(2), Jun. 2001, pp. 390-391 and 398-399.

News Release from Sandia National Laboratories, www.sandia.gov/media/NewsRel/NR2001, Jun. 25, 2001, pp. 1-3.

"GTS Advances on Cold Spray Technology," *Journal of Thermal Spray Technology*, vol. 10(3), Sep. 2001, pp. 434-435.

"Selected Abstracts of Thermal Spray Literature," *Journal of Thermal Spray Technology*, vol. 10(3), Sep. 2001, pp. 532-538.

*Journal of Thermal Spray Technology*, vol. 10(4), Dec. 2001, pp. 555-558, 562, 565, 566, 568-571.

"Selected Abstracts of Thermal Spray Literature," *Journal of Thermal Spray Technolgoy*, vol. 10(4), Dec. 2001, pp. 673-691.

*Journal of Thermal Spray Technology*, vol. 11(1), Mar. 2002, pp. 13-14, 27-28.

Yang, Y., et al., "Deposition of highly adhesive $ZrO_2$ coating on Ti and CoCrMo implant materials using plasma spraying," Biomaterials 24 (2003), pp. 619-627.

Donadille, C., et al.; "Overview No. 82—Development of Texture and Microstructure During Cold-Rolling and Annealing of F.C.C. Alloys: Example of an Austenitic Stainless Steel," *Acta metall.*, vol. 37, No. 6, 1989, pp. 1547-1571.

McCune, R.C., et al.; "An Exploration of the Gold Gas-Dynamic Spray Method for Several Materials Systems," *Proceedings of the 8th National Thermal Spray Conference*—Houston, Texas, Sep. 11-15, 1995, pp. 1-5.

Khor, K.A., et al.; "The Thermal Spray Processing of HA Powders and Coatings," *Journal of Materials*, The Metallurgical Society, Feb. 1997, pp. 51-57.

Wilcox, B.A.; "Report on: Conference on Thermal Spray Processing of Nanoscale Materials, Davos, Switzerland, Aug. 4-7, 1997," *European Materials Science and Engineering—Office of Naval Research—European Office*, Sep. 18, 1997.

Sampath, S., et al.; "Thermal-Spray Processing of Materials," *MRS Bulletin*, Jul. 2000, pp. 12-16.

Herman, H., et al.; "Thermal Spray: Current Status and Future Trends," *MRS Bulletin*, Jul. 2000, pp. 17-25.

Fincke, J. R., et al.; "Advanced Diagnostics and Modeling of Spray Processes," *MRS Bulletin*, Jul. 2000, pp. 26-31.

Beach, et al., *Xylylene Polymers*, Encyclopedia of Polymer Science and Engineering, vol. 17, Second Edition, pp. 990-1025, 1989.

Bull, Parylene Coating for Medical Applications *Medical Product Manufacturing News*, Mar. 1993 (2 pages).

C.R. Bard, Pe Plus Peripheral Balloon Dilatation Canadatheter, *C. R. Bard, Inc.*, Aug. 1985.

Casper, et al., Fiber-Reinforced Absorbable Compsite for Orthopedic Surgery, *Polymeric Materials Science and Engineering*, Proceedings of the ACS Division of Polymeric Materials: Science and Engineering, vol. 53, Fall Meeting 1985.

Charlson, et al., Temperature Selective DEPOosition of Parylene-C, *IEEE Transactions on BiomediCanadal Engineering*, vol. 39, No. 2, pp. 202-206, (Feb. 1992).

Charnsangavej, C., M.D., et al., Endovascular Stent for Use in Aortic Dissection: an in Vitro Experiment, *Radiology*, pp. 323-324, vol. 157, No. 2, Nov. 1985.

Cragg, Andrew, M.D., et al., Nonsurgical Placement of Arterial Endoprostheses: A New Technique Using Nitinol Wire, *Radiology Journal*, April 1983, pp. 261-263.

De Scheerder, et al., Biocompatibiity of Polymer-Coated Oversized Metallic Stents Implanted in Normal Porcine Coronary Arteries, *Atherosclerosis*, vol. 114, pp. 105-114 (1995).

Dotter, Charles T., Transluminal Expandable Nitinol Coil Stent Grafting: Preliminary REPOort, *Radiology Journal*, pp. 259-260, Apr. 1983.

Dotter, Charles T., Transluminally-Placed Coilspring Endarterial Tube Grafts: Long-Term Patency in Canine Popliteal Artery, *Investigative Radiology*, Sep./Oct. 1969, pp. 329-332.

Duprat, et al., Flexible Balloon-Expanded Stent for Small Vessels, *Radiology Journal*, pp. 276-278, 1987.

Eskin, et al., Growth of Cultured Canadalf Aortic Smooth Muscle Cells on Cardiovascular Prosthetic Materials, *Journal of BiomediCanadal Material Research*, vol. 10, pp. 113-1 22 (1976).

Gebelein, et al., (ed.) Biomedical and Dental Applications of Polymers, *Polymer Science and Technology*, vol. 14, pp. 143-161 (No date).

Gengenbach, et al., Evolution of the Surface Composition and Topography of Perfluorinated Polymers Following Ammonia-Plasma Treatment, *Plasma Surface ModifiCanadation of Polymers*, pp. 123-146.

Gölander, et al., RF-Plasma-Modified Polystyrene Surfaces for Studying Complement Activation, *J. Biomater. Sci. Polymer Edn.*, vol. 4, No. 1, pp. 25-30 (1992).

Hahn, et al., *Glow Discharge Polymers as Coatings for Implanted Devices*, John M. Dlaton Research Center, University of Missouri-Columbia and the Graduate Center for Materials Research, pp. 109-113 (1981).

Hahn, et al., Biocompatibility of Glow-Discharge-Polymerized Films and Vacuum-DEPOosited Parylene, *Journal of Applied Polymer Science: Applied Polymer Symposium* 38, 55-64 (1984).

Hollahan, et al. *Attachment of Amino Groups to Polymer Surfaces by Radiofrequency Plasmas, Journal of Applies Polymer Science*, vol. 13, pp. 807-816 (1969).

Inagaki, et al., Hydrophilic Surface Modification of Polyethylene by No-Plasma Treatment, *Adhesion Science Technology*, Nov. 1989, vol. 4, No. 2, pp. 99-107.

*Information Regarding Parylene-C Coating for ACS Metal Stent*, In-Home Memorandum fron Ed Newton to Mike Clayman, Dennis Houlsby and Joe Tartaglia, Oct. 15, 1993 attaching Parylene, a Biostable Coating for MediCanadal AppliCanadation by Roger Olson.

ISEEE Transactions on Biomedical Engineering, Vol. BME-27, No. 11, Nov. 1980(5 pages).

Kelley B.S., et al., Totally Resorbable High-Strength Composite Material, *Advances in Biomedical Polymers*, Edited by Charles G. Gebelein (1987).

Lambert, et al., Lolized Arterial Wall Drug Delivery From a Polymer-Coated Removable Metallic Stent, *Circulation*, vol. 90, No. 2 pp. 1003-1011 (Aug. 1994).

Loeb, et al., *Parylene as a ChroniCanadally Stable, REPOroducible Microelectrode Insulator*, IEEE Transactions on BiomediCanadal Engineering, pp. 121-128 (Mar. 1977).

Loh, et al., Plasma Enhanced Parylene DEPOosition, *Antec*, pp. 1099-1103 (1991).

Maas, D., et al., Radiological Follow-Up of Transluminally Inserted Vascular Endoprostheses: An Experimental Study Using Expanding Spirals, *Radiology Journal*, SEPOtember 1984, pp. 659-663, vol. 152, No. 3.

Mirich, et al., Percutaneously Placed Endovascular Grafts for Aortic Aneurysms: Feasibility Study, *Radiology*, 1989, Part 2, pp. 1033-1037.

Moody: Vacuum Coating Ultrasonic Transducers, *Sensors*, Dec. 1993 (1 page).

Muller, et al., Advanced in coronary Angioplasty: Endovascular Stents, *Coronary Artery Disease*, vol. 1, No. 4, Jul./Aug. 1990.

Nichols, et al., *Electrical Insulation of Implantable Devices by Composite Polymer Coatings*, Dalton Research Center, University of Missouri, 1987.

Nova Tran™ Custom Coating Services, Parylene Conformal Coating, Brochure, Union Carbide (8 pages).

70th Scientific Assembly and Annual Meeting: Scientific Program, *Radiology*, Washington, DC: Nov. 25-30, 1984, Special Edition, vol. 153(P).

Olson, Parylene, *A Biostable Coating for Medical Applications*, for Nova Tran Parylene Coating Services (Jul. 25, 1988; Nov. 14, 1988).

Palmaz, et al., Expandable Intraluminal Graft; a Preliminary Study, *Radiology Journal*, pp. 73-77, 1985.

The Parylene Press (A Publication of Specialty Coating Systems, Inc.), Winter 1992 (7 pages).

The Parylene Press (A Publication of Specialty Coating Systems, Inc.), Spring 1993 (6 pages).

The Parylene Press (A Publication of Specialty Coating Systems, Inc.), Summer 1993 (4 pages).

Parylene Conformal Coatings Specifications and Properties, Sales Brochure, Union Canbide Specialty Coating Systems (12 pages).

Parylene Environmentally Compatible Conformal Coatings for Electronic Components Assemblies and Precision Parts, Brochure, Union Carbide Electronics Division (14 pages).

Parylene and Nova Tran™ Parylene Coating Services, for Unmatched Conformal Coating Performance, Brochure, Union Carbide Specialty Coating Systems (21 pages).

Parylene, a Biostable Coating for MediCanadal Applications, Brochure, Union Carbide Specialty Coating Systems (6 pages).

Typical Parylene Properties, Printout, Para Tech Coating Company; Lab Top® Parylene DEPOosition System Model 3000, Sales Brochure, Para Tech Coating Company (7 pages).

Program: Day 2 (Nov. 18) the Radiological Society of North America, *Radiology*, 1985.

72nd Scientific Assembly and Annual Meeting: RSNA Scientific Program, *Radiology*, Nov. 30-Dec. 5, 1986, Special Edition vol. 161(P).

Rösch, Josef, M.D., et al., *Gianturco Expandable Stents in Experimental and Clinical Use*, paper presented at The Twelfth Annual Course on "Diagnostic Angiography and Interventional Radiology" Mar. 23-26, 1987 (San Diego, California).

Rösch, JosEPOh, M.D., et al., Gianturco Expandable Wire Stents in the Treatment of Superior Vena Canadava Syndrome Recurring after Maximum-tolerance Radiation, *Cancer*, pp. 1243-1 246, vol. 60, SEPOtember 1987.

Rösch, J., M.D., et al., Transjugular IntrahEPOatic Portacaval Shunt: an Experimental Work, *The American Journal of Surgery*, pp. 588-592, vol. 121, May 1971.

Sadhir, et al., The Adhesion of Glow-Discharge Polymers, Silastic and Parylene to Implantable Platinum Electrodes: Results of Tensile Pull Tests After Exposure to Isotonic Sodium Chloride, vol. 2, *Biomaterials*, pp. 239-243 Oct. 1981.

Schmidt, et al., *Long-Term Implants of Parylene-C Coated Microelectrodes, Medical & Biological Engineering and Computing*, pp. 96-101 (Jan. 1988).

Union Carbide Technology Letter, New Busiiness DEPOartment—Parylene, Oct. 1973, No. 7 (8 pages).

Union Carbide, Electronic Materials, Parylene Products, Oct. 1973, No. 9 (23 pages).

Union Carbide Technology Letter, May 1974, No. 11(12 pages).

Union Carbide Technology Letter, Oct. 1975, No. 15 (13 pages).

Union Carbide, Electronic Materials, Parylene Products, Mar. 1976, No. 16 (4 pages).

Union Carbide, Electronic Materials, Parylene Products, Aug. 1977, No. 18 (7 pages).

Union Carbide, Electronic Materials, Parylene Products, Oct. 1977, No. 1, Revision 2 (7 pages).

Union Carbide, Electronic Materials, Parylene Products, Oct. 1977, No. 2, Revision 1 (9 pages).

Union Carbide, Electronic Materials, Parylene Products, Oct. 1977, No. 3 (21 pages).

Union Carbide, Electronic Materials, Parylene Products, Oct. 1977, No. 4 (13 pages).

Union Carbide, Electronic Materials, Parylene Products, Oct. 1977, No. 6 (12 pages).

Union Carbide, Electronic Materials, Parylene Products, Oct. 1977, No. 7, Revision 1 (8 pages).

Union Carbide, Electronic Materials, Parylene Products, Oct. 1977, No. 8, Edited (19 pages).

Union Carbide, Electronic Materials, Parylene Products, Oct. 1977, No. 10 (50 pages).

Union Carbide, Electronic Materials, Parylene Products, Oct. 1977, No. 11 (12 pages).

Union Carbide, Electronic Materials, Parylene Products, Oct. 1977, No. 12, Revision 1 (6 pages).

Union Carbide, Electronic Materials, Parylene Products, Oct. 1977, No. 13, Revision 1 (7 pages).

Union Carbide, Electronic Materials, Parylene Products, Oct. 1977, No. 14, Revision 1 (11 pages).

Union Carbide, Electronic Materials, Parylene Products, Oct. 1977, No. 15, Revision 1 (8 pages).

Union Carbide, Electronic Materials, Parylene Products, Oct. 1977, No. 17, Revision 1 (11 pages).

Union Carbide, Electronic Materials, Parylene Products, Jan. 18, 1982, No. 5, Revision 4 (17 pages).

Union Carbide A-174 Silane, Sales Brochure, Union Carbide Adhesion Promoters, Jan. 1968 (5 pages).

Wallace, Michael J., et al., Tracheobronchial Tree: Expandable Metallic Stents Used in Experiemental and Clinical Applications (Work in Progress), *Radiology*, pp. 309-312, vol. 158, Feb. 1986.

Wong, et al., An Update on Coronary Stents, *Cardio*, Feb. 1992.

Wright, et al., Percutaneous Endovascular Stents: an Experimental Evaluation, *Radiology Journal*, pp. 69-72, 1985.

Yoshioka, et al., Self-expanding Endovascular Graft: an Experimental Study in Dogs, *American Journal of Roentgeriology*, pp. 673-676, vol. 151, Oct. 1988.

Yoshioka, et al., Development And Clinica lApplication of Biliary Endoprostheses Using Expandable Metallic Stents, *Japan Radiological Society*, 1988, vol. 48, No. 9, pp. 1183-1185 (with translation).

Yuen, et al., *Tissue Response to Potential Neuroprosthetic Materials Implanted Subdurally, Biomaterials*, vol. 8, pp. 57-62, Mar. 1987.

* cited by examiner

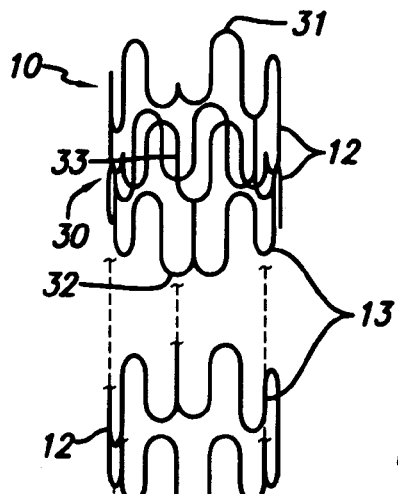
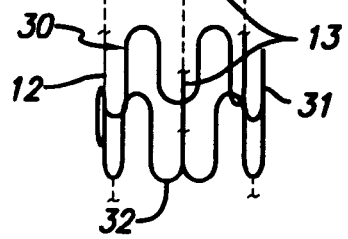
FIG. 14
FIG. 15
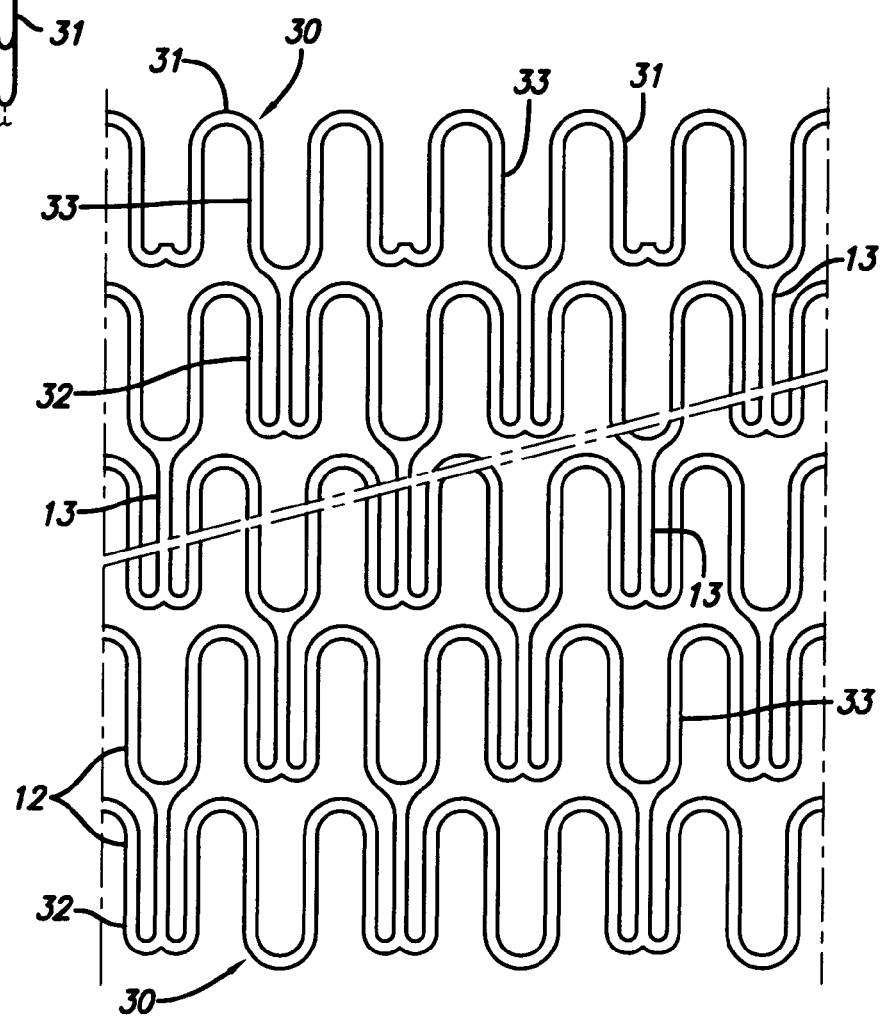

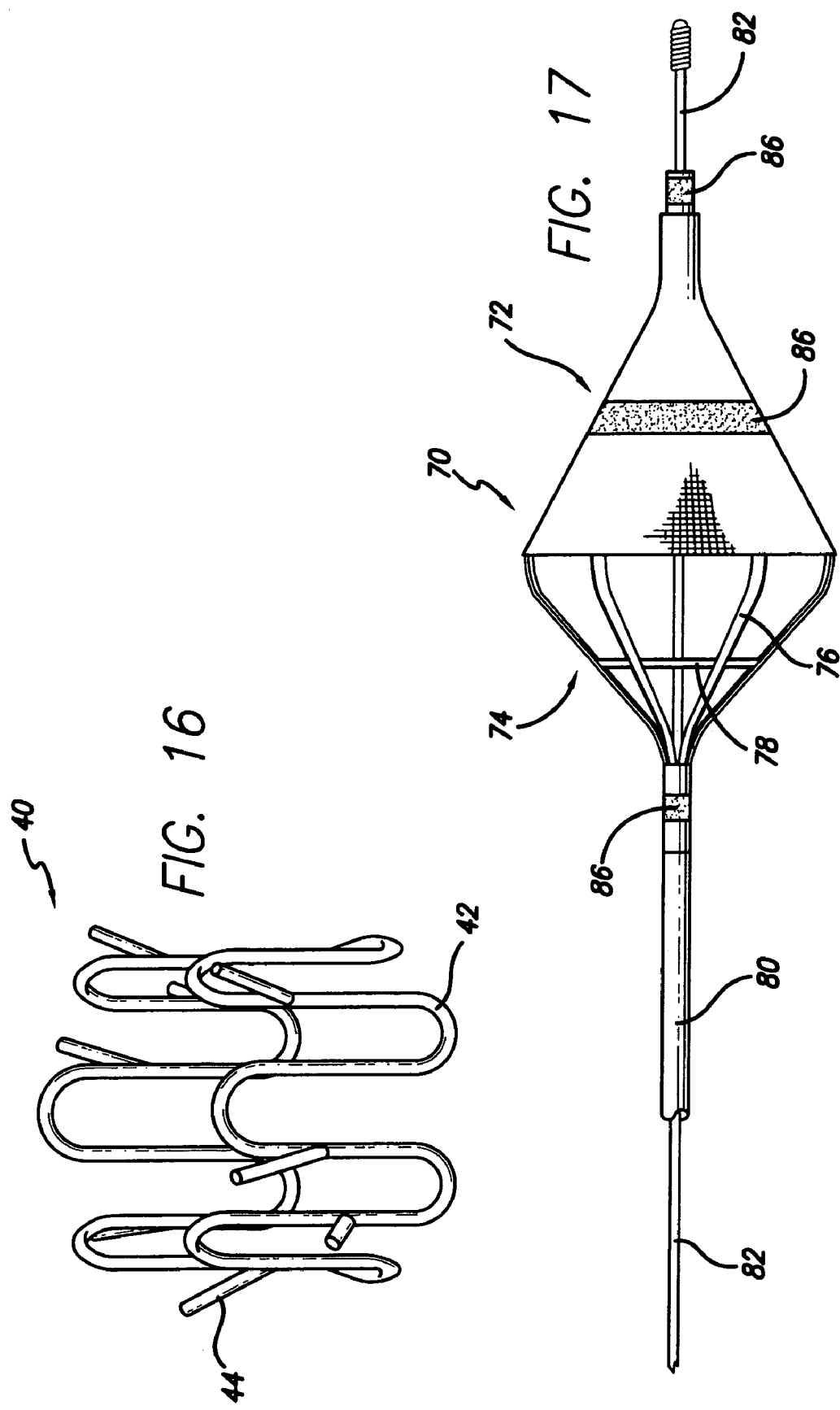

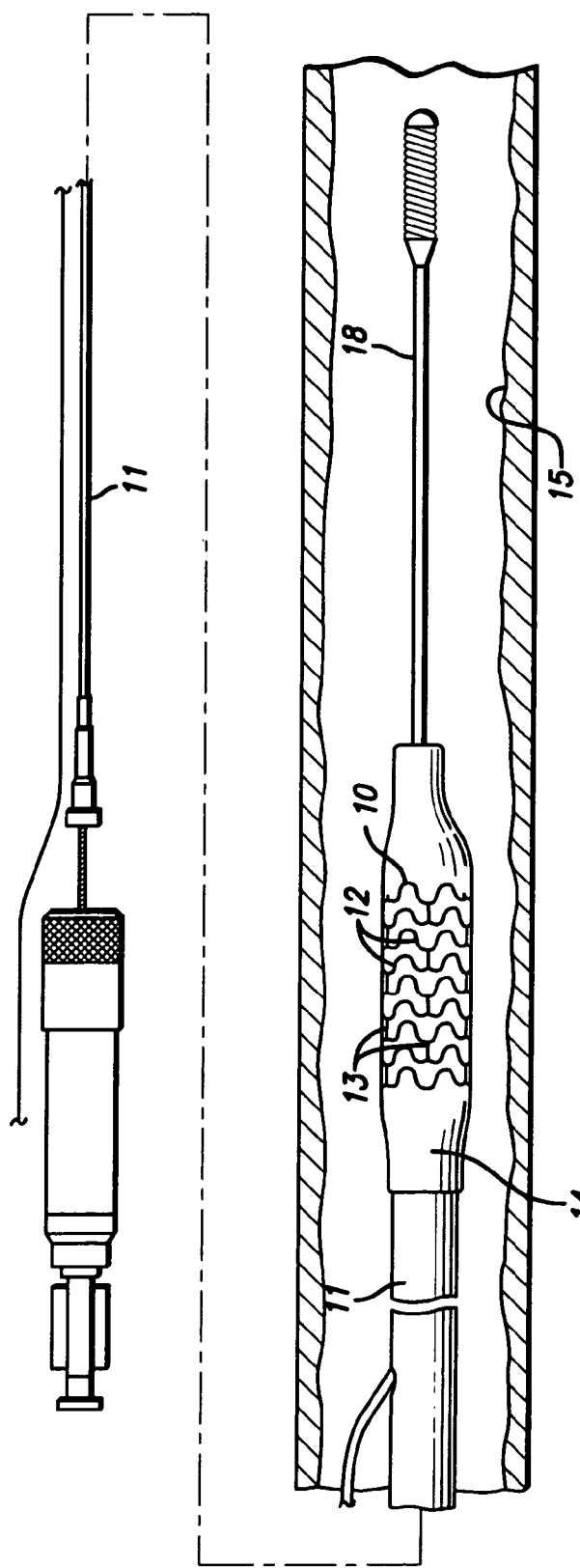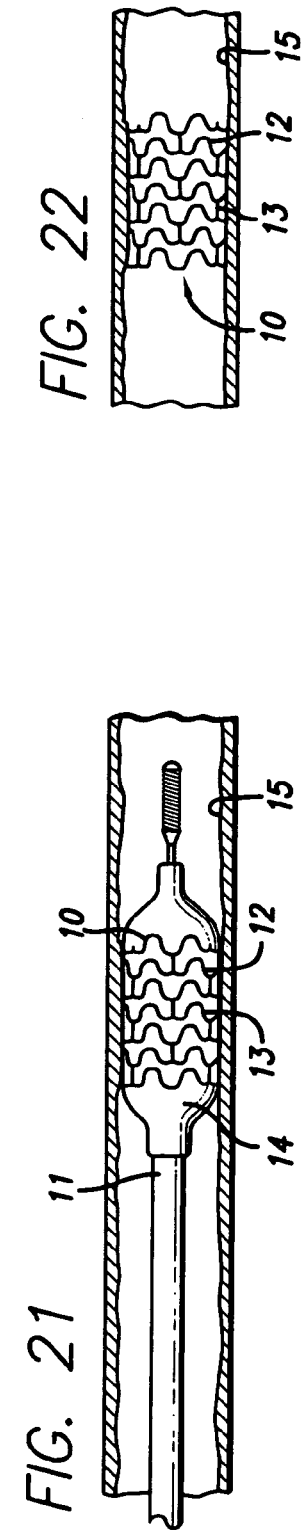

METHOD AND APPARATUS FOR SPRAY PROCESSING OF POROUS MEDICAL DEVICES

CROSS-REFERENCE TO RELATED APPLICATIONS

This application is a divisional of U.S. application Ser. No. 10/331,838, filed Dec. 30, 2002, now U.S. Pat. No. 7,163,715, which is a continuation-in-part of U.S. application Ser. No. 09/880,514, filed Jun. 12, 2001, now U.S. Pat. No. 7,201,940, the contents of each of which are hereby incorporated herein by reference.

BACKGROUND OF THE INVENTION

This invention relates to medical devices, and more particularly to methods of manufacturing and coating medical devices utilizing thermal spray processing and cold spray processing. The medical devices may be made porous to act as a functional drug delivery vehicle.

Several interventional treatment modalities are presently used for heart disease, including balloon and laser angioplasty, atherectomy, and by-pass surgery. A focus of recent development work in the treatment of heart disease has been directed to endoprosthetic devices referred to as stents. Stents are generally cylindrically shaped intravascular devices that are placed within an artery to hold it open. The device can be used to reduce the likelihood of restenosis and to maintain the patency of a blood vessel immediately after intravascular treatment. In some circumstances, a stent can also be used as the primary treatment device where the stent is expanded to dilate a stenosis and then left in place.

Many medical devices, including stents, are manufactured from commercially available metals and metal alloy substrates, such as stainless steel and cobalt based alloys, configured as tube stock, wherein the substrate typically has average grain sizes ranging from approximately 0.0025 inch (64 microns), ASTM grain size 5, to around 0.00088 inch (22 microns), ASTM grain size 8. These grain sizes typically result in about two to five grains across the thickness of the device. Part of the limitation in achieving a finer grain size with metals and metal alloys arises from the number of draws and anneals the substrate must go through to achieve its final size. Stents and other medical devices (such as guide wires, ring markers, pacemaker lead tips, and catheters) may benefit from a reduction in grain size of the substrate.

Intravascular interventional devices, such as stents, are typically implanted within a vessel in a contracted state, and expanded when in place in the vessel in order to maintain the patency of the vessel. Such medical devices may have a metallic support structure to provide the strength required to maintain the patency of the vessel in which it is to be implanted so as to allow fluid flow through the vessel. Such metallic medical devices are often provided with an exterior surface coating with the purpose of providing a more biocompatible and/or hemocompatible surface. Since it is often useful to provide localized therapeutic pharmacological treatment of a blood vessel at the location being treated with the medical device, it has been the practice within the medical industry to configure such implantable medical devices with a coating of a polymeric material having the capability of being loaded with antiproliferative drugs and other therapeutic agents. Such polymer coated medical devices provide for the placement and release of therapeutic drugs at a specific intravascular site, but are relatively expensive and difficult to manufacture using conventional processes.

What has been needed and heretofore unavailable in the art of manufacturing medical devices, such as stents, configured from commercially available biocompatible materials, such as stainless steel and cobalt-based alloys, are methods for forming porous implantable medical devices and for forming a porous coating on consolidated medical devices. In addition, it would be desirable to form drug-eluting medical devices without the need for coating the substrate with a polymer. The present invention meets these and other needs.

SUMMARY OF THE INVENTION

The present invention relates to methods of manufacturing porous medical devices utilizing thermal spray processing and cold spray processing. Conventional spray processes are adapted to manufacture porous substrates and coatings that may be constructed as tube stock, metallic sheet, wire or near net-shaped configurations for forming drug-eluting medical devices, such as, but not limited to, stents, anastomosis clips, embolic protection filters, graft attachment systems, ring markers, guide wires, mitral valve repair devices, tubular or wire based implants, defibrillator or pacemaker lead tips, and catheters or other delivery system devices. As part of the spray process or as a separate aspect of the method of manufacture of the medical device, a therapeutic agent or drug may be applied to the porous coating or substrate.

Thermal spray processing and spray processing provide methods for manufacturing a porous medical device for use as a drug delivery vehicle in three ways: by forming porous starting materials, by spraying consolidated starting materials with a porous coating, and by spraying near net-shaped medical devices with a porous coating. Current thermal and cold spray processes inherently include a degree of porosity that are supplemented with post-processing techniques that provide full consolidation of the sprayed material. However, the present invention takes advantage of the spray process to create a desired level of porosity so as to produce substrates and coatings that can elute a drug. The spray process may incorporate a wide variety of materials, such as metals, metal alloys, polymers, ceramics, cermets and composites. Furthermore, the conditions of the spray process may be varied to achieve desired properties for a particular material, for example, to minimize oxidation or other contamination. In addition, the present invention provides for the manufacture of a medical device configured for drug delivery without the need for triple-coating the substrate with a polymer. Thus, a polymer topcoat may or may not be needed with porous medical devices manufactured by spray processes of the present invention.

Hypotubing or other tube stock manufactured using the spray processes of the present invention may be configured into a stent or other tubular medical device. The porous medical device may then be impregnated with a therapeutic agent or drug via known or to be developed transport mechanisms, such as soaking in a solution having an effective concentration of the drug or agent. The spray process may be designed to provide a multiple gradient of porosity through and/or within the material, e.g., denser on the outer diameter of a stent so the drug releases preferentially into the artery wall, or denser then more porous then denser again through the device thickness to allow the material itself to act as a diffusion barrier for the release of the drug. The process could also potentially spray different materials into the different layers, so long as the corrosion and mechanical properties of the manufactured stent were not adversely affected. For example, the base layer of the medical device could be metallic with an outer layer being formed from a sprayed ceramic, wherein either the base layer and/or the coating may be porous.

Alternatively, a spray process of the present invention may be used to coat existing tube stock or starting materials for further processing into a medical device, such as a stent. This inventive coating process has the advantage that soaking the porous coated medical device in a drug would limit the drug coating to the outer diameter only of the medical device, thereby minimizing drug release into the bloodstream. The coating may be composed from a material of the same composition as the underlying substrate or may be composed of a different material, such as a ceramic, hat would not adversely affect the corrosion or mechanical functionality of the end product. One aspect of the present invention contemplates that the drug-eluting edical device is formed at least in part of a metallic material, for example, iron, obalt, platinum, titanium, and their alloys.

Another aspect of the present invention includes coating a near net-shaped medical device formed by conventional manufacturing methods. A coating formed by the spray process of the present invention may be metallic, ceramic, or any other material that can undergo the thermal or cold spray process successfully. Such a coated medical device may be impregnated with a therapeutic agent or drug via a known or to be developed transport mechanism. A drug or agent that could withstand the temperature/pressure of the spray process could be sprayed directly onto the medical device with the coating material. A further aspect of the present invention includes using the spray process to form functionally graded coatings so that the sprayed material acts as a controlling diffusion barrier to drug release. The process may provide an all-over coating or a coating focusing only on the outer diameter and sidewalls of the medical device, thereby allowing preferential focusing of the delivery of a drug or therapeutic agent.

The therapeutic agents and drugs that may be loaded into the drug-eluting porous medical device of the present invention can include antiplatelets, anticoagulants, antifibrins, antiinflammatories, antithrombins, and antiproliferatives. Such drugs and agents are most often used to treat or prevent restenosis, and are provided by way of example and are not meant to be limiting, since other types of therapeutic agents which are equally applicable for use with the present invention may be incorporated in a porous medical device formed by spray processing.

Other features and advantages of the invention will become apparent from the following detailed description, taken in conjunction with the accompanying drawings, which illustrate, by way of example, the features of the invention.

DESCRIPTION OF THE DRAWINGS

FIG. 14 depicts a perspective and exploded view of an unexpanded stent embodying the present invention.

FIG. 15 depicts a plan view of a flattened section of the stent shown in FIG. 14 so as to illustrate the undulating pattern of the stent.

FIG. 16 depicts a longitudinal plan view of an anastamosis device made in accordance with the present invention.

FIG. 17 depicts a longitudinal plan view of an embodiment of an expanded embolic protection device made in accordance with the present the invention.

FIG. 20 depicts a longitudinal plan view of a stent delivery catheter assembly made in accordance with the present invention, wherein the stent has been positioned proximate to a lesion within a cross-section of a patient's blood vessel.

FIG. 21 depicts a longitudinal plan view of the distal end of a stent delivery catheter assembly made in accordance with the present invention, wherein the balloon and stent are in an expanded state within a cross-section of a patient's blood vessel.

FIG. 22 depicts a longitudinal plan view of a stent made in accordance with the present invention, wherein the stent has been expanded and remains within a cross-section of a patient's blood vessel.

DETAILED DESCRIPTION OF THE PREFERRED EMBODIMENTS

The present invention relates to use of various spray processes for forming porous starting materials and porous near net-shaped medical devices, and to provide a porous coating on starting materials or near net-shaped medical devices. In accordance with the present invention, thermal spraying and/or cold spraying may be used to partially or wholly form starting materials, such as, but not limited to, tube stock, substrate sheets and wire, which can be further processed into a net-shaped (finished) medical devices. Similarly, thermal spraying and/or cold spraying may be used to coat starting materials or to coat near-net-shaped medical devices, such as, but not limited to, stents, anastomosis clips, embolic protection filters, graft attachment systems, markers, guide wires, mitral valve repair devices and defibrillator lead tips. As part of the spray process or as a separate aspect of the method of manufacture of the medical device, a therapeutic agent or drug may be applied to the porous coating or substrate. While virtually any medical device that is implanted or used in the body will benefit from the present invention, the embodiments disclosed herein as applied to stents are intended as only examples and are not meant to be limiting.

Figure 4:
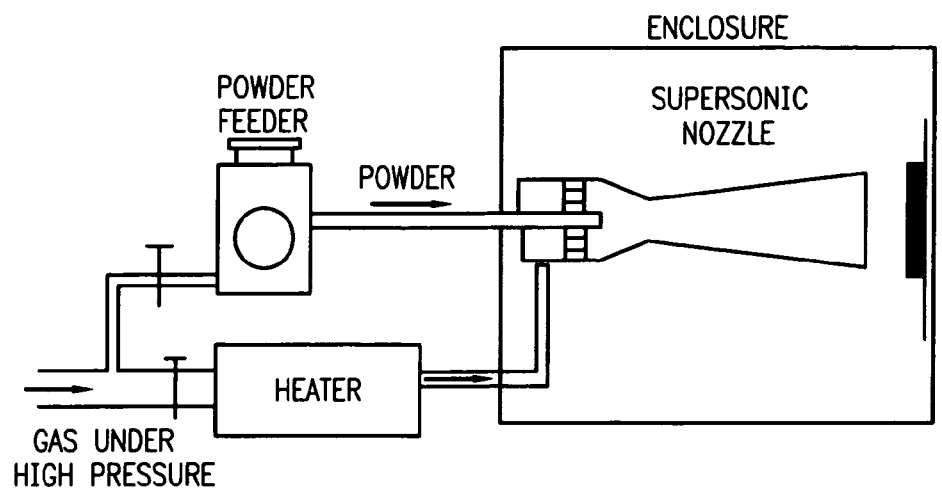
FIG. 4 depicts a schematic diagram of a cold spray processing apparatus.

Spray processing (thermal spraying and cold spraying) provides methods for manufacturing a porous medical device for use as a drug delivery vehicle in three ways: (1) creating porous tube stock (e.g., hypotubing) or other starting material via thermal or cold spraying; (2) spraying pre-existing starting materials (e.g., tube stock or metallic sheets) with a porous coating; and (3) spraying pre-existing medical devices (e.g., stents) with a porous coating. The various spray processes can utilize a wide variety of materials, and the conditions of the process may be varied depending on the material to minimize oxidation or other contamination. As used herein, thermal spray processing refers to a group of known metallurgical spray processes, such as, but not limited to, combustion (wire and powder), arc wire, high velocity oxy-fuel (HVOF), plasma and detonation (see FIGS. 5-10). As used herein, cold spray processing refers to recently developed processes in which lower temperatures and higher velocities (versus those used in thermal spray processing) are used to impinge the material onto a substrate or mandrel (FIG. 4).

Both the processes of thermal spraying and cold spraying inherently have porosity as a difficulty to overcome, and while current methods allow up to full (one-hundred percent) consolidation of the sprayed material, the present invention produces a porous coating or porous substrate that can elute a drug or therapeutic agent. A potential exists for drug co-spraying with the coating or substrate material, so long as the drug does not degrade at the high temperatures and/or velocities used in the spray process. As desired, a polymer or similar topcoat to protect or control the release of the therapeutic agent or drug could be applied to the medical device via a spray process, so long as the polymer would not degrade from the processing.

Starting materials, such as tube stock (hypotubing) or substrate sheets may be manufactured using a spray process. The starting material may then be processed into a medical device (stent), and the porous material may be impregnated with a therapeutic agent or drug via known or to be developed transport mechanisms, such as soaking in or spraying with a solution having an effective drug or agent concentration. For purposes of the present invention, the term "impregnate" means to fill throughout or to saturate. The spray process may be varied to allow a multiple gradient of porosity through and/or within the material, e.g., denser on the inner diameter or layers (so the drug releases preferentially into the artery wall for a stent), or denser—then more porous—then denser again to allow the material itself to act as a diffusion barrier for the release of the therapeutic agent or drug. The process could also potentially spray different materials into the different layers, so long as the corrosion and mechanical properties of the manufactured medical device were not adversely affected. For example, the base layer(s) of the medical device could be formed from a metal or alloy, while the outer layer(s) of the medical device may be formed from a ceramic material.

The spray process of the present invention may also be used to coat existing starting materials for medical devices, such as tube stock, hypotubing and sheets of a substrate material for further processing into a medical device, such as a stent. Use of a spray process has the advantage that soaking the porous coated medical device in a therapeutic agent or drug would limit the drug or therapeutic agent to the outer surface of the medical device, minimizing release of the drug or agent into the bloodstream. The coating may be made from a material of the same composition of the underlying starting material (e.g., a metallic alloy), or may be made from other material (e.g., a ceramic) that would not adversely affect the corrosion or mechanical functionality of the end product. As with forming starting materials, the spray process of the present invention could be used to produce functionally graded coatings (e.g., different degrees of density and porosity) so as to allow the coating material to create a diffusion barrier to control the release of the therapeutic agent or drug.

The spray process of the present invention may be used to coat a near net-shaped medical device, such as an existing stent. Such a coating could be metallic, ceramic, composite, polymeric or any other material that can undergo the spray process successfully. The coated medical device would then be impregnated with a drug or therapeutic agent via known or to be developed transport mechanisms. Alternatively, the drug or agent could be co-sprayed with the coating material, so long as there is minimal resulting degradation. Thus, a therapeutic agent or drug that could withstand the temperature and pressure of the spray process could be applied directly onto the existing medical device with the coating material. A special fixture may be constructed to hold the medical device and prevent damage during the coating process. As with coating starting materials, the spraying could be functionally graded to allow the material to act as a controlling diffusion barrier to drug release. The spraying could consist of an all-over coating or a coating focusing only on the outer surface or diameter of the medical device and any sidewalls when an inert material, such as a ceramic were used, allowing preferential focusing of the drug delivery. For example, a stent made from 31 6L stainless steel could be layered with a porous coating of a ceramic and then impregnated with paclitaxel. The drug coated stent could then be further coated with a protective polymer layer.

As used herein, spray processing describes a broad class of related processes in which molten (or semi-molten) droplets or fine particles of a metal, metal alloy, ceramic, glass, polymer and/or other suitable material are (1) sprayed to form a starting material (e.g., a tube stock or flat sheet); (2) sprayed onto a surface of a previously formed substrate material (e.g., hypotube or sheet metal) to produce a coating; or (3) sprayed onto a near-net-shape product. The spray process provides the medical device with unique properties, such as strain-tolerant composites or porous materials susceptible to impregnation with a therapeutic agent or drug. Deposition rates via spray processes are very high in comparison to alternative coating technologies, providing deposit thicknesses commonly in the range of about 0.1 to 1.0 millimeter (mm). Furthermore, thicknesses greater than one centimeter (cm) can be achieved with some materials. Two types of spray process compatible with the present invention include thermal spray processing and cold spraying.

Some advantages of using a spray process to form a porous medical device include the versatility with respect to feed materials (metals, ceramics, and polymers in the form of wires, rods, or powders); the capacity to form barrier and functional coatings on a wide range of substrates; the ability to create freestanding structures for net-shape manufacturing of high performance ceramics, composites, and functionally graded materials; and the rapid solidification synthesis of specialized materials. Further, the spray process can be used to manufacture a net or near net-shaped medical device, such that the product resulting from the spray process is close to or at the desired size and shape of the final product. Spray processing is presented here both with and without post-processing of the sprayed material.

There are many possible variations of known spray process for forming porous starting materials and porous coatings resulting in medical devices of the present invention. Because porous starting materials and coatings may be used in conjunction with medical devices that are generally cylindrical in shape, the spray processes may incorporate either a moving spray gun and/or a moving mandrel or substrate so as to uniformly disperse material onto the mandrel to form the porous starting material or porous coating. The spray processes used in the present invention may be enhanced through the use of a precision computer controlled apparatus.

Another benefit of using a spray process to manufacture a medical device is that the spray process may be used to form porous tube stock on top of a removable mandrel. The porous tube stock formed by a spray process can be used in place of a gun drilled or extruded rod, and eliminates the need for subsequent tube manufacturing.

The thickness of the tube stock may be varied by spraying more or less material, and the inner diameter dimensions may be varied by changing the size of the mandrel. The inner mandrel may be made of a substance that melts out, or that is coated with a substance that allows easy removal of the finished sprayed tube stock. If the grain size, porosity, and dimensional tolerances (including wall runout, wall thickness, concentricity and surface roughness) are within specifications, the mandrel may be removed and the sprayed tube stock may subjected to further processing into a stent or other tubular or ring-shaped product. To create a ring-shaped product from a tube stock, the tube is sprayed to the desired dimensions and then cut in the transverse direction to result in rings of the desired size.

For removal of the porous tube stock after it is formed, it may be beneficial to either melt or shrink the mandrel's diameter to ease removal of the tube stock. For example, the mandrel can be formed of metal that will shrink in diameter when cooled, while the tube stock may be heated so that it expands radially outwardly. The mandrel can then be easily removed from the tube stock. The mandrel and tube stock may also both be heated so that the difference in expansion rates may cause separation between the two. The mandrel may also be removed from the tube stock by a process called "cross-rolling." The tube stock, with the mandrel inside, can be run through a series of crossed rollers that will flex the tube stock and impart a separation between the tube and the mandrel, which is then easily removed. Alternatively, the mandrel could be lubricated so as to provide a low friction surface from which to slide the off tube stock.

Any of several known or to be developed post-processing operations may be performed on a porous tube stock formed from a spray process so as to improve or otherwise modify grain size, porosity, and final dimensions and tolerances of the sprayed tube stock. The inner diameter dimensions and surface finish of the porous tube stock may be dependant on the mandrel that is used. If the starting size of the sprayed tube is large enough, it may be desirous to bore and ream or just ream the inner diameter for both dimension and surface roughness improvement. A drawing operation may be performed on the sprayed tube to achieve the desired final size. In addition, if the outer diameter is too rough, the tube stock may be machined or ground prior to the drawing operation. Further, the tube stock may be mechanically processed or swaged before the tube stock is removed from the mandrel in order to develop desired mechanical properties. After the tube stock is removed from the mandrel other post processing includes exerting high mechanical pressures onto the stent in order to develop the desired mechanical properties and tempering and hardening the tube stock with traditional heat treating mechanisms known in the art. For correct sizing, the outer diameter and/or the inner diameter of the tube stock can be machined, reamed, ground, or drawn to size after being removed from the mandrel. The grain size of the porous tube stock may be decreased by reducing the required number of heat-processing steps or by reducing the starting size of the raw material that is spray processed to form the tubing.

Any of several known or to be developed post-processing operations may also be performed on a porous coating formed on a medical device from a spray process so as to improve or otherwise modify grain size, porosity, and final dimensional tolerances of the sprayed medical device. Further, the thickness of the coating may be varied by spraying more or less material, and may be varied along the length and around the diameter of the object to be-coated. If a porous coating is formed by spray processing the inner diameter of tube stock or other tubular near net-shaped devices (such as stents), then post-processing may include modifying the inner diameter dimensions and surface roughness by, for example, boring and/or reaming. If the porous coating is formed by spray processing an outer wall or surface of the medical device, post-processing may include machining (e.g., centerless grinding) or drawing to reduce coating thickness variability and to improve the surface finish. When the grain or node size, material density, porosity and dimensional tolerances of the porous coating are within desired specifications, the porous coated medical device may be subjected to post-passivation or other desired post spray processing steps when the coating process is an intermediate step in finishing the medical device.

While spray processing may be used to manufacture near-net shape medical devices, the variability in the spray process may require post-processing so that the product achieves the required dimensional tolerances. Any of several known or to be developed post-processing operations may be performed on a porous medical device formed from a spray process so as to improve or otherwise modify grain size, porosity, and final dimensional tolerances of the sprayed medical device. Such processing may include machining, centerless grinding, heat treating or other surface processing of the outer wall or surface of the sprayed medical device to reduce wall thickness variability and to improve the surface finish.

Two aspects of using spray processing to create porous medical devices of the present invention include (1) controlling the grain size of the sprayed material, and (2) controlling the degree of porosity in the sprayed substrate or coating.

The grain size or node size of the sprayed material used in porous starting materials or sprayed porous coatings resulting from the present invention depends on numerous factors, including the size of the particles being sprayed; the grain size of the particles; the formation, impact and rate of solidification of the sprayed particles; and the length of time the particle material is heated above a temperature that allows significant grain growth. Grain-size strengthening is where there is an increase in strength of a material due to a decrease in the grain size. A larger grain-boundary area resulting from smaller grain sizes more effectively blocks dislocation movement. The type and amount of working required to achieve a desired grain size depends on the material being sprayed, for example, ceramics may require a high temperature working step, and metals and composites may be workable at room temperature.

For a metallic tube, if the grain size is larger than desired, the tube may be swaged to introduce heavy dislocation densities, then heat treated to recrystallize the material into finer grains. Alternatively, different material forms may be taken through a drawing or other working and heat treating process to recrystallize the tubing. The outer diameter of the tube usually requires a machining step to smooth the surface after the swaging process, and the same may be true before the tubing can be properly drawn.

For a metallic coating, one modification to grain size that may be made is to heat-treat the coating to control grain growth. For example, it may be desirable to spray a metallic coating onto a target substrate, heat the coating, and then grow the metallic grains in the coating. Similarly, the porous coated substrate may be mechanically processed or swaged, annealed, heat-treated, or cross linked in order to develop desired mechanical properties. Generally, it is difficult to work a porous, coated substrate in a way that introduces a high dislocation density that may then be used to recrystallize the material. For a spray coated metallic wire or tubing, the wire or tubing may be swaged or drawn to produce a higher dislocation density, then annealed to recrystallize to a smaller grain size. Porous ceramic coatings formed from a spray process may require post-processing heating to control grain size; whereas, porous polymeric coatings may require further cross-linking.

Lowering the grain size and increasing the number of grains across the thickness of the porous medical device allows the grains within the medical device to act more as a continuum and less as a step function. For example, spray processing 31 6L stainless steel to a smaller grain size may result in an average grain size of between approximately one and sixty-four microns, with a subsequent average number of grains across the strut thickness about eight or greater. With a well controlled spray process, it is possible to reduce the average grain size of a porous medical device formed from spray processed 31 6L stainless steel to between one and ten microns.

The mechanics and chemistry of spray processing inherently results in small voids (porosity) in the sprayed material. The porosity of the sprayed material may be maximized, minimized, eliminated or controlled to a desired level through adjustment of the spray process parameters, such as particle size, temperature, pressure, injection velocity and co-spraying with a binder material that may be subsequently removed. In addition, the porous medical device may be post-processed to further control the size and distribution of the pores and voids. One such method of post processing to control porosity is to process the material under high mechanical pressure in a vacuum to sinter the grains together, as is generally used for powder processing. Additional methods to control porosity include co-spraying with varying amounts of a binder material that may be removed through subsequent operation, such as sublimation or soaking in a solvent.

The process of manufacturing porous starting materials, porous coatings and porous near net-shaped medical devices in accordance with the present invention requires selecting a spray process method and apparatus, such as cold spraying, combustion spraying, arc spraying, high velocity oxy-fliel spraying and plasma spraying. The spray process selected must be compatible with the material to be sprayed, such as metals, alloys, polymers, ceramics, and cermets. Similarly, the same or an additional spray process could be selected for spraying of a drug or therapeutic agent, such as antiplatelets, anticoagulants, antifibrins, antiiflammatories, antithrombins, and antiproliferatives.

Figure 1:
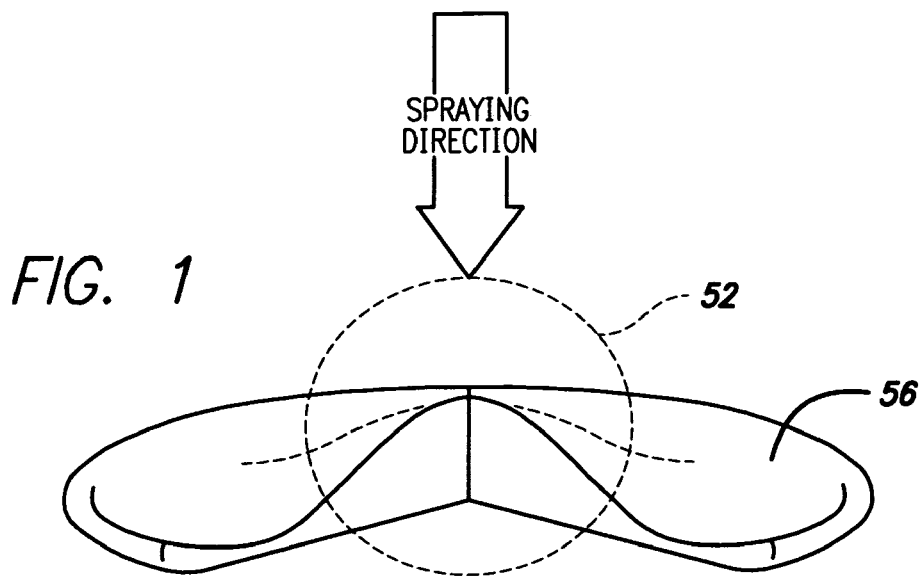
FIG. 1 depicts a schematic diagram of a spherical particle impinged onto a flat substrate so at to create a splat.
Figure 2:
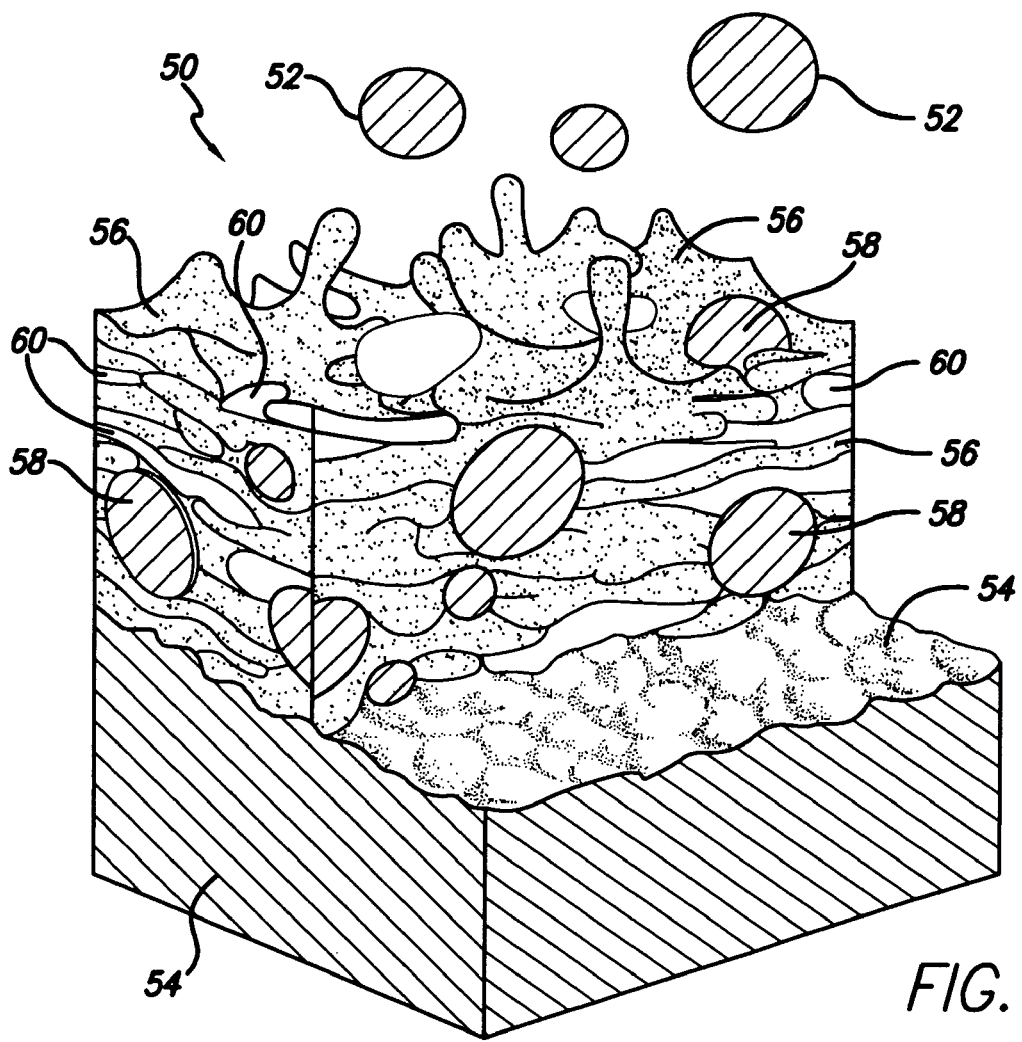
FIG. 2 depicts a schematic diagram of a porous spray coating.
Figure 3:
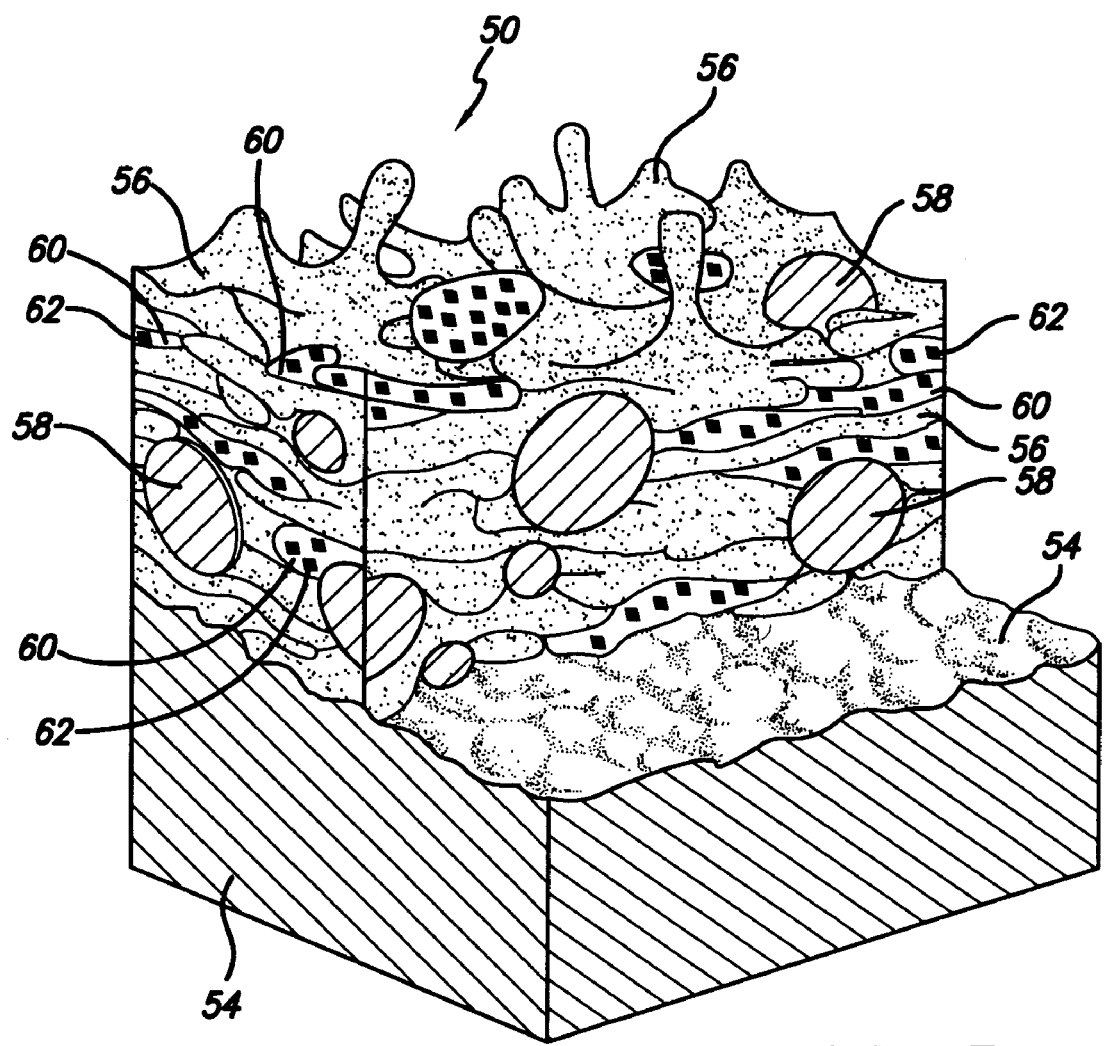
FIG. 3 depicts a schematic diagram of a porous spray coating containing a drug or therapeutic agent.

Referring to FIGS. 1-3, an aspect of each spray process includes forming a deposit 50 by directing a particle 52 of the source material towards a mandrel or substrate 54. Depending on the spray process selected, the particle may be in a molten, semi-molten or solid state. When the particle contacts the mandrel or substrate, the particle tends to flatten to form a splat 56 (FIG. 1), which adheres or otherwise bonds to the mandrel or substrate. The resulting spray deposit is generally composed of cohesively bonded splats, that result from the high velocity impact, spreading, deformation and/or rapid solidification of a high flux of particles. The physical properties and behavior of the deposit depend on many factors, including the cohesive strength among the splats, the size and morphology of the porosity, oxidation of the starting material, the occurrence of cracks and defects within the deposit, and the grain structure of the source material within the splats. In addition, some rogue particles 58 may not form splats upon contact with the substrate or newly formed splats and may generally retain their original shape, e.g., spherical.

As shown in FIG. 2, the deposit 50 may be formed with considerable pores or voids 60, thereby creating a porous deposit in accordance with the present invention. The amount of voids or degree of porosity may be controlled during the spray process or during post-processing steps as heretofore described. One or more drugs or therapeutic agents 62 may be applied to the porous deposit by a variety of known or to be developed process, such a soaking or dipping the porous tube stock, substrate sheet, medical device or the like in a solution or bath of the drug or therapeutic agent. Similarly, the drug or therapeutic agent may be sprayed on the coating after the spraying of the starting material or at the same time as spraying the starting material (co-spraying). The spray process for applying the drug or agent to the porous deposit may be one of the spray processes described herein, or a lower temperature and/or reduced velocity (lower pressure) process so as to prevent or reduce degradation of the active ingredient in the drug or agent. The result of the present inventive method is a drug impregnated porous coating or substrate, as shown in FIG. 3.

Materials used in the spray process can include elements (e.g., metals), metallic alloys (e.g., iron-based, cobalt-based, titanium-based), ceramics, composites, cermets and polymers. Suitable biocompatible materials for use in forming medical devices using the spray process of the present invention include, but are not limited to, elements and alloys of titanium, tungsten, tantalum, vanadium, gold, silver, palladium, platinum and iridium. Certain biocompatible metal alloys that have been used in forming medical devices include:

(1) iron-carbon alloys, e.g., ASTM F 138, ASTM P139, AISI 31 6L (18Cr-14Ni-2.5 Mb);

(2) cobalt-chromium alloys, e.g., ASTM F90 (Co-2OCr-20W-1ONi) [available as trade name products HAYNES 25 (Haynes) and L-605 (Carpenter)], ASTM F562 (35Co-35Ni-2OCr-1OMo) [available as trade name product MP35N(SPS Technologies)], ASTM F 1058 (4OCo-2OCr-1 6Fe-1 5Ni-7Mo) [available as trade name products ELGILOY (Elgin) and PHYNOX (Imphy Ugine Precision)], HAYNES 188 (Haynes) (Co-24Ni-23Cr-15W); and (3) nickel-titanium alloys, e.g., ASTM F2063 [nitinol available from Wah Chang and Special Metals].

Suitable biocompatible polymers that may be used in the spray process as part of the substrate, coating or topcoat include, but are not limited to polymethyl-methacrylate (PMMA), ethylenevinylalcohol (EVAL), polybutyl-methacrylate (PBMA), biodegradable polymers [such as polyglycolic acid (PGA) and polyL-lactic acid (PLLA)], copolymers and blends thereof.

Various therapeutic agents, drugs and other pharmacologic compounds may be applied to the porous substrate or porous coating to control local thrombosis and restenosis. Classes of such compounds include, but are not limited to, substances that are antiproliferative, antithrombogenic, antineoplastic, antiinflammatory, antiplatelet, anticoagulant, antifibrin, antithrombin, antimitotic, antibiotic, and antioxidant. Specific examples of therapeutic agents or drugs that are suitable for use in accordance with the present invention include taxol, paclitaxel, docetaxel, sirolimus, everolimus, actinomycin D (ActD), prostaglandins, aspirin or derivatives and analogs thereof.

Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein Jib/lila platelet membrane receptor antagonist, recombinant birudin, thrombin inhibitor (available from Biogen located in Cambridge, Mass.), and 7E-3B (an antiplatelet drug from Centocor located in Malvern, Pa.). Examples of antimitotic agents include methotrexate, azathioprine, vincristine, vinblastine, fluorouracil, adriamycin, and mutamycin.

Examples of cytostatic or antiproliferative agents include angiopeptin (a somatostatin analog from Ibsen located in the United Kingdom), angiotensin converting enzyme inhibitors such as CAPTOPRIL (available from Squibb located in New York, N.Y.), CILAZAP'RIL (available from Hoffman-LaRoche located in Basel, Switzerland), or LISINOPR.IL (available from Merck located in Whitehouse Station, N.J.), calcium channel blockers (such as nifedipine), coichicine, fibroblast growth factor ("FGF") antagonists, fish oil (omega 3-fatty acid), histamine antagonists, LOVA-STATIN (an inhibitor of HMG-CoA reductase, a cholesterol lowering drug from Merck), methotrexate, monoclonal antibodies [such as platelet-derived growth factor ("PDGF") receptors], nitroprusside, phosphodiesterase inhibitors, prostaglandin inhibitor (available from GlaxoSmithKline located in United Kingdom), seramin (a PDGF antagonist), serotonin blockers, steroids, thioprotease inhibitors, triàzolo-pyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents are known in the art. The calculation of dosages, dosage rates and appropriate duration of treatment are previously known in the art. Furthermore, the therapeutic drugs or agents are applied to the porous substrate or coating or as part of the spray process at desired concentration levels per methods well known in the art.

As mentioned above, spray processing includes several variants of the apparatus and spraying method, such as cold spraying, combustion spraying, arc spraying, high velocity oxy-fliel spraying and plasma spraying. The following is a brief summary of the basic components and functions of several of the spray processes that may be used to manufacture porous starting materials, coatings and near net-shaped medical devices in accordance with the present invention.

As shown in FIG. 4, cold spray processing provides a manufacturing process for expanding the operational window for coating and forming medical devices from biocompatible materials that are deposited with much lower thermal exposure than encountered with traditional thermal spray processes. The cold spray process exploits properties of gas dynamics that permit supersonic gas streams and attendant particle velocities to be obtained. In addition, the cold spray process permits a high degree of spatial control by virtue of the gas nozzle characteristics and generally short standoff distances that can be employed. This results in a uniform structure of the coating or spray-formed substrate with a substantially preserved formation of powder material without phase transformations and hardening, i.e., the coatings applied do not crack, and their corrosion resistance, microhardness, and cohesion and adhesion strengths are enhanced.

The cold spray process involves minimal heat input to the feedstock powder or the substrate, thus making it possible to deposit thermally sensitive as well as conventional materials. The process generally produces high density, low residual stress deposits with low oxide contents. When the cold spray process is used to produce a consolidated coating or substrate, an average grain size of between one and sixty-four microns may be achieved. Alternatively, the cold spray process parameters may be controlled to produce porous coatings and substrates that are suitable as a drug delivery vehicle. In addition, a robust drug or therapeutic agent may be co-sprayed with the biocompatible material.

Cold spray processing may be used to project biocompatible materials onto a surface at relatively lower temperatures than used in thermal spray processing, and the materials typically are not sprayed in a molten or semi-molten state. Instead, the biocompatible material is sprayed as powder particles, which are introduced from a feeder into a high pressure gas (1.5 to 2.5 MPa) where both the gas and particles enter a supersonic nozzle or jet. The particle size may range from about one to sixty-four microns for consolidated spray coatings, and may be varied to achieve a desired degree of porosity. The gas is typically heated to a temperature from about 380° to 420° Celsius. Suitable gases for creating a jet stream (300-1500 m/sec) with the powder particles include, but are not limited to, air, nitrogen ($N_2$), oxygen ($O_2$), helium (He), argon (Ar), xenon (Xe), and carbon dioxide ($CO_2$). The jet stream is directed against a mandrel or substrate positioned about eight to ten millimeters from the nozzle so as to coat the mandrel or substrate with particle splats, as shown in FIGS. 1-3. Finally, the spray-formed substrate or coated medical device is removed from the mandrel or other holding mechanism for further post-processing, as described herein.

Typical values for tensile adhesion of consolidated cold spray coatings are in the range of 30-80 MPa (4.4-11.6 ksi), with porosities in the range of one to ten volume percent, deposit thicknesses ranging from ten microns to ten millimeters, deposition rates in the range of 0.0 10 to about 0.080 m3 per hour, and deposition efficiencies in the range of fifty to eighty percent. Several considerations when using a cold spray process include the dependency of porosity on the ambient spray environment, powder characteristics (e.g., particle size and size distribution), and thermal-spray parameters (e.g., powder level, gas-flow features, and spray distance). The spray environment will have a significant influence on, for example, the oxidation of metals, leading to greater porosity.

Figure 5:
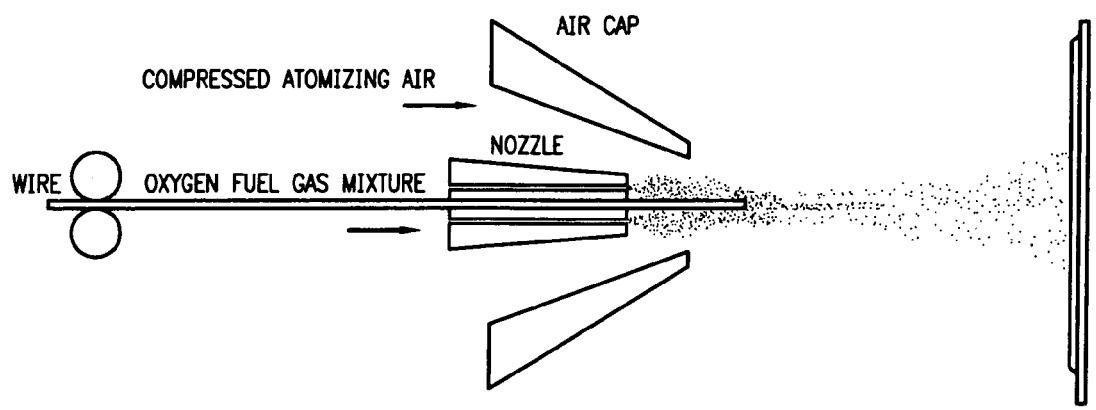
FIG. 5 depicts a schematic diagram of a combustion wire thermal spray processing apparatus.

As shown in FIG. 5, combustion wire thermal spray processing includes spraying molten metal or other biocompatible material onto a surface to form a substrate or a coating. First, the material in wire form is melted in a flame (oxyacetylene flame is the most common) and atomized using compressed air or other gas to form a fine spray. When the atomized spray contacts a prepared substrate or mandrel, the fine molten droplets rapidly solidify and form the desired substrate or coating. The temperature of a target near net-shaped medical device can be maintained relatively low during processing, thereby avoiding damage, metallurgical changes and distortion to the substrate material. The parameters of the combustion wire thermal spray process (e.g., temperature, particle size, and gas velocity) can be adjusted to control the porosity of the spray-formed substrate or coating.

Figure 6:
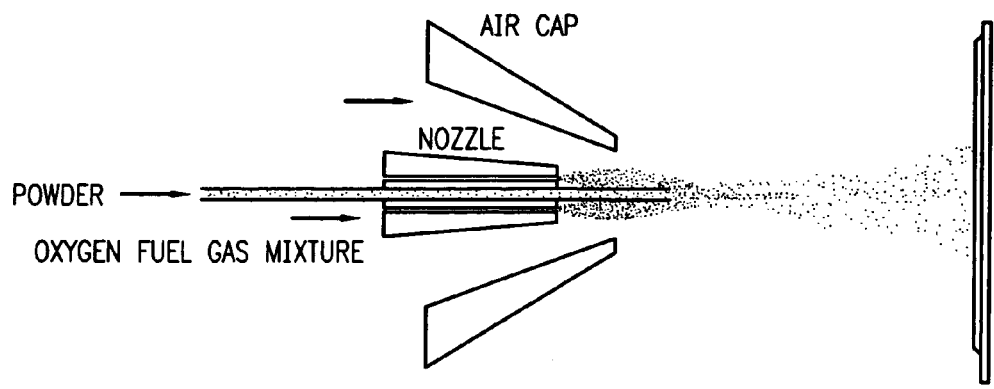
FIG. 6 depicts a schematic diagram of a combustion powder thermal spray processing apparatus.

As shown in FIG. 6, combustion powder thermal spray processing includes spraying molten material onto a mandrel or near a net-shaped medical device to provide a spray-formed substrate or a coating. In combustion wire spray processing there is a wide range of materials that can be easily processed into powder form, providing a larger choice of coatings. The process, however, is limited by materials with higher melting temperatures than the flame can provide or if the material decomposes on heating. The biocompatible powder is propelled and melted into the flame (most commonly oxy-acetylene or hydrogen) to form a fine spray. When the spray contacts a prepared substrate material, the fine molten droplets rapidly solidify and form the desired substrate or coating. The temperature of a target near net-shaped medical device can be maintained relatively low during processing, thereby avoiding damage, metallurgical changes and distortion to the substrate material. The parameters of the combustion powder thermal spray process (e.g., temperature, particle size, and gas velocity) can be adjusted to control the porosity of the spray-formed substrate or coating. In addition, a robust drug or therapeutic agent able to withstand the high temperatures used in the process may be co-sprayed with the biocompatible material.

Figure 7:
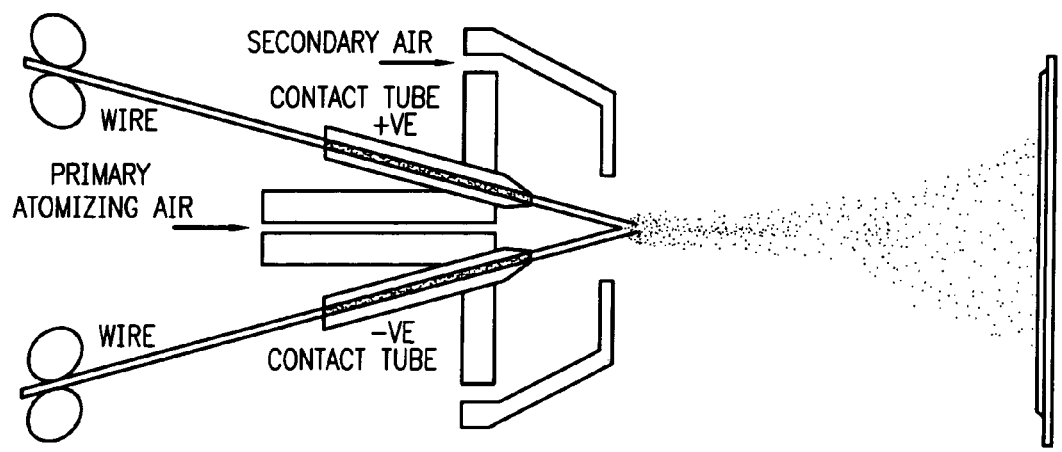
FIG. 7 depicts a schematic diagram of an arc wire thermal spray processing apparatus.

Referring to FIG. 7, the arc wire spray process utilizes a pair of electrically conductive wires formed from a biocompatible material that are melted by an electric arc created between the two wires. The molten material is atomized by compressed gas and propelled towards the surface of a mandrel or near net-shaped medical device. The molten particles rapidly solidify on impact to create a spray-formed substrate or coating. The temperature of a target near net-shaped medical device can be maintained relatively low during processing, thereby avoiding damage, metallurgical changes and distortion to the substrate material. The parameters of the arc wire thermal spray process (e.g., temperature particle size, and gas velocity) can be adjusted to control the porosity of the spray-formed substrate or coating. Benefits from using the arc wire apparatus for spray processing include low capital investment, simplicity of operation, and high deposit efficiency. Benefits of arc spray substrates and coatings include high bond strength and density, low internal stresses, high thickness capability and high quality microstructures.

Figure 8:
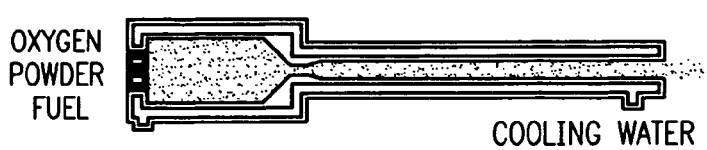
FIG. 8 depicts a schematic diagram of an HVOF thermal spray processing apparatus.

As shown in FIG. 8, high velocity oxygen fuel (HVOF) thermal spray processing is similar to the combustion powder spray process (FIG. 6), except that HVOF utilizes extremely high spray velocities. There are a variety of HVOF apparatus (guns) that use different methods to achieve high velocity spraying. One system incorporates a high pressure, water-cooled combustion chamber and a long nozzle. Fuel (e.g., kerosene, acetylene, propylene and hydrogen) and oxygen are fed into the chamber, and the combustion produces a hot, high pressure flame that is forced down a nozzle, thereby increasing its velocity. Biocompatible material (e.g., metals and metal alloys) in powder form may be fed axially into the combustion chamber under high pressure or fed through the side of a laval type nozzle, where the pressure is lower. The gas and particle velocity exiting an HVOF gun can be in excess of 2500 feet per second. Further, the gas temperature is usually very high, ranging from 2500° to 4500° F. The velocity of the biocompatible material particles causes friction through kinetic energy when the particles make contact with a mandrel or the substrate of a near net-shaped medical device. Such high energy can aid in the melting and adhesion of the particles to the mandrel or device so as to deposit a spray-formed substrate or coating.

Another known HVOF system uses a simpler combination of a high pressure combustion nozzle and an air cap. Fuel gas (e.g., propane, propylene or hydrogen) and oxygen are supplied at high pressure, and combustion occurs outside the nozzle and within an air cap supplied with compressed air. The compressed air pinches and accelerates the flame, and acts as a coolant for the gun. Biocompatible material in powder form is fed at high pressure axially from the center of the nozzle towards a mandrel or near net-shaped medical device so as to deposit a spray-formed substrate or coating.

Benefits of HVOF include high particle velocity, low particle temperatures, and reduced time at temperature during the spraying process, which reduces oxidation and degradation of the constituents. The temperature of a target near net-shaped medical device can be maintained relatively low during processing, thereby avoiding damage, metallurgical changes and distortion to the substrate material. The parameters of the HVOF spray process (e.g., temperature, particle size, and gas velocity) can be adjusted to control the porosity of the spray-formed substrate or coating. In addition, a robust drug or therapeutic agent able to withstand the high temperatures and velocities used in the process may be co-sprayed with the biocompatible material.

Figure 9:
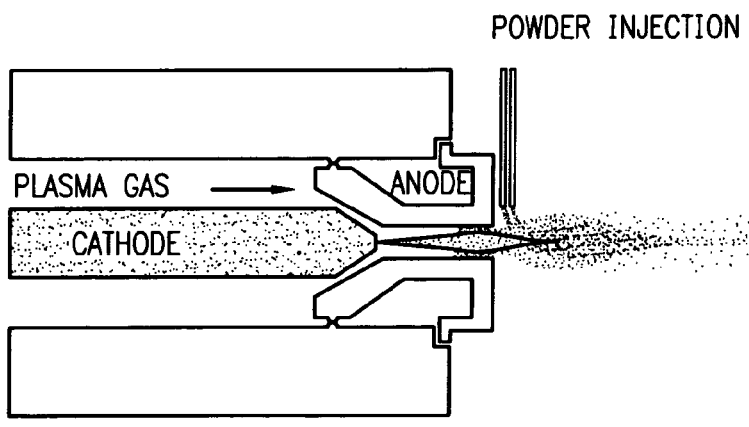
FIG. 9 depicts a schematic diagram of a plasma thermal spray processing apparatus.

Referring to FIG. 9, the plasma spray process involves spraying molten or heat softened biocompatible material onto a mandrel or the substrate of a near net-shaped medical device to provide a porous spray-formed substrate or a porous coating. Biocompatible material in the form of powder is injected into a very high temperature plasma flame, where it is rapidly heated and accelerated to a high velocity. The hot material impacts on the mandrel or substrate surface and rapidly cools to solidify and form the desired substrate or coating. The temperature of a target near net-shaped medical device can be maintained relatively low during processing, thereby avoiding damage, metallurgical changes and distortion to the substrate material. The parameters of the plasma spray process (e.g., temperature, particle size, and gas velocity) can be adjusted to control the porosity of the spray-formed substrate or coating. In addition, a robust drug or therapeutic agent compatible with the plasma process may be co-sprayed with the biocompatible material.

The plasma spray apparatus (gun) may be constructed of a copper anode and tungsten cathode, both of which may be water cooled. Plasma gas (e.g., argon, nitrogen, hydrogen, helium) flows around the cathode and through the anode, which is shaped as a constricting nozzle. The plasma is initiated by a high voltage discharge, which causes localized ionization and a conductive path for a direct current (DC) arc to form between cathode and anode. The resistance heating from the arc causes the gas to reach extreme temperatures, dissociate and ionize to form plasma. Typically, plasma generation begins at 10,000 F, and most plasma guns maintain an internal temperature between 15,000° F. and 30,000° F. The plasma exits the anode nozzle as a free or neutral plasma flame (i.e., plasma that does not carry electric current). When the plasma is stabilized and ready for spraying, the electric arc extends down the nozzle, instead of shorting out to the nearest edge of the anode nozzle. This stretching of the electric arc is a result of a thermal pinch effect.

Due to the tremendous heat generated with this thermal spray process, the plasma gun components must be constantly cooled with water to prevent the gun from melting. Water may be sent to the gun through the same lines as electrical power. Small temperature changes in the cooling water may affect the ability to produce high quality, plasma generated spray coatings and substrates. Accordingly, a water chiller can be used to help produce high quality porous medical devices. Cold gas around the surface of the water-cooled anode nozzle, being electrically non-conductive, constricts the plasma arc, raising its temperature and velocity. Powder is fed into the plasma flame most commonly via an external powder port mounted near the anode nozzle exit. The powder is so rapidly heated and accelerated that spray distances can be on the order of twenty-five to one hundred-fifty millimeters. Benefits associated with a plasma spray process include a high degree of flexibility, a large choice of substrate and coating materials, high production spray rates, and automation of the process.

Figure 10:
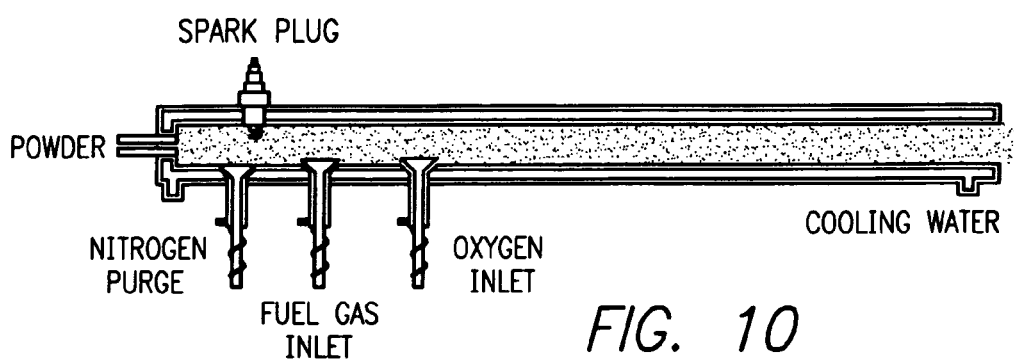
FIG. 10 depicts a schematic diagram of a detonation thermal spray processing apparatus.

As shown in FIG. 10, a detonation thermal spray apparatus (gun) is configured with an elongate water-cooled barrel having inlet valves for receiving gases and biocompatible material as a powder. Oxygen and fuel (acetylene is the most common) are fed into the barrel along with a charge of powder. A spark is used to ignite the gas mixture, and the resulting detonation heats and accelerates the powder to supersonic velocity down the barrel so as to impact on a mandrel or near net-shaped medical device. A pulse of nitrogen is used to purge the barrel after each detonation. This detonation process is repeated many times a second. The high kinetic energy content powder particles provide a deposit of a very dense and strong spray-formed substrate or coating. The parameters of the detonation thermal spray process (e.g., temperature, particle size, fuel type) can be adjusted to control the porosity of the spray-formed substrate or coating. In addition, a robust drug or therapeutic agent compatible with the detonation process may be co-sprayed with the biocompatible material.

Figure 11:
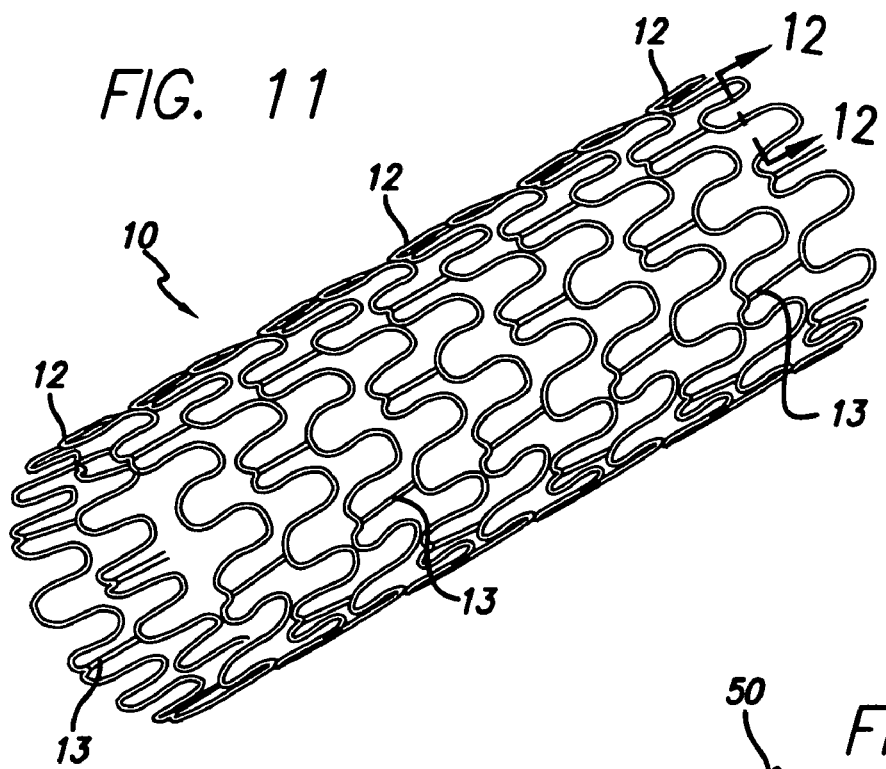
FIG. 11 depicts a perspective view of an embodiment of a stent made in accordance with the present invention.

Referring now to FIG. 11, and by way of example, the present invention may be incorporated into a stent or similar endoprosthesis 10. Such a stent may be balloon expandable or self-expanding. Such stents may be made of any suitable biocompatible material as heretofore described. Such a stent may be of a ring 12 and link 13 pattern or other configurations, such as, but not limited to a zigzag design, a coil design or tubular mesh design, as known in the art or to be determined in the future. The stent may be formed from porous tube stock or porous substrate sheets using a spray process of the present invention. Similarly, the stent may be formed as a porous near net-shaped device. Alternatively, the stent may be manufactured from non-porous starting materials (e.g., consolidated tube stock) using conventional techniques, and then covered with a porous coating, using the materials and spray processes described herein.

Figure 12:
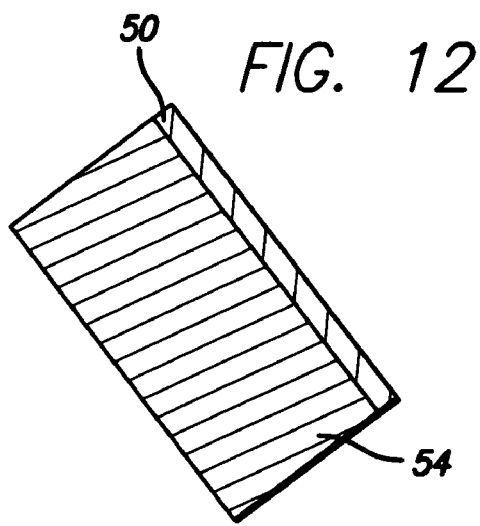
FIG. 12 depicts a cross-sectional view along lines 12-12 of FIG. 11 showing a coating made in accordance with the present invention.
Figure 13:
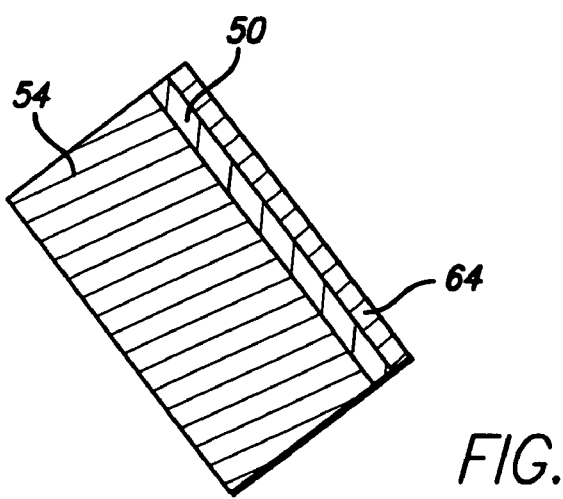
FIG. 13 depicts an alternate view of FIG. 12, including an external layer over the coating.

Referring to FIGS. 12 and 13, the stent 10 may include porous coating or deposit 50 disposed on the outside of the base material or substrate 54. Alternatively, the porous deposition layer may be embedded between the base layer and an outer layer 64 of the stent. The outer layer of the stent may be the same material as the base layer, or may be of another material, such as a more biocompatible metal, a polymer or a drug delivery component. Further, the coating or deposition layer may be impregnated with a drug or therapeutic agent. A modification after the coating is applied may include varying the radial thickness of the coating around the stent. Accordingly, the radial-thickness can either be varied around the diameter or along the length of the stent. Alternatively, the coating thickness may be varied as part of the spray process.

In one embodiment as shown in FIGS. 14 and 15, the stent 10 is configured with links 13 between adjacent radially expandable rings 12. Each pair of links on one side of a ring may be circumferentially offset from the pair on the other side of the ring. Such a configuration results in a stent that is longitudinally flexible in essentially all directions. As best observed in FIG. 15, the rings may be in the form of a serpentine pattern 30. The serpentine pattern may be configured with a plurality of U-shaped members 31, W-shaped members 32, and Y-shaped members 33, each having a different radius so that expansion forces are more evenly distributed over the various members. Other stent patterns can be formed by utilizing the processes of the present invention, and the embodiments illustrated in FIGS. 11-15 are by way of example and are not intended to be limiting.

For use in coronary arteries, the stent diameter must be very small, so the tube stock from which it is made must necessarily also have a small diameter. Typically, the stent has an outer diameter on the order of about 0.03 inch (0.75 mm) to about 0.06 inch (1.5 mm) in the unexpanded condition, equivalent to the tubing from which the stent is made, and can be expanded to an outer diameter of 0.10 inch (2.5 mm) or more. The wall thickness of the tubing is about 0.002 inch (0.05 mm) to about 0.01 inch (0.25 mm). As with the foregoing stent dimensions, all of the medical devices that can be formed utilizing the present invention can vary substantially in size and shape so that the disclosed dimensions and shapes are representative examples only and are not meant to be limiting.

The spray process of the present invention may also be used to form an anastomosis device (clip) 40, as shown in FIG. 16. The body 42 and the attachment portions 44 of the device may be formed from spray-formed tube stock, wire or the like. Similarly, the anastomosis device may be formed as a spray-formed near net-shaped device. Alternatively the body and/or the attachment portions of the device may be coated using the spray processes and biocompatible materials disclosed herein. Further, a drug or therapeutic agent may be applied to a porous base material or coating. Various shapes and configurations of anastomosis devices may be formed or coated in accordance with the present invention.

Referring now to FIG. 17, and by way of example, the present invention may be incorporated into an embolic protection device 70. Such a device may include a spray-formed filter assembly 72 and a spray-formed expandable strut assembly 74. The embolic protection device may further include an elongate tubular member 80, within which may be disposed a spray-formed guidewire 82 for positioning the device within a corporeal lumen. In accordance with the present invention, the embolic protection device may include a plurality of marker bands 86, which may be constructed from spray-formed material. The expandable strut assembly may include struts 76, 78, which may be spray-formed in accordance with the present invention. Alternatively the filter assembly, strut assembly, tubular member and/or guidewire may be coated using a spray process as heretofore described. The entire embolic protection device or portions thereof may be made porous and/or impregnated with a drug or therapeutic agent.

Figure 18:
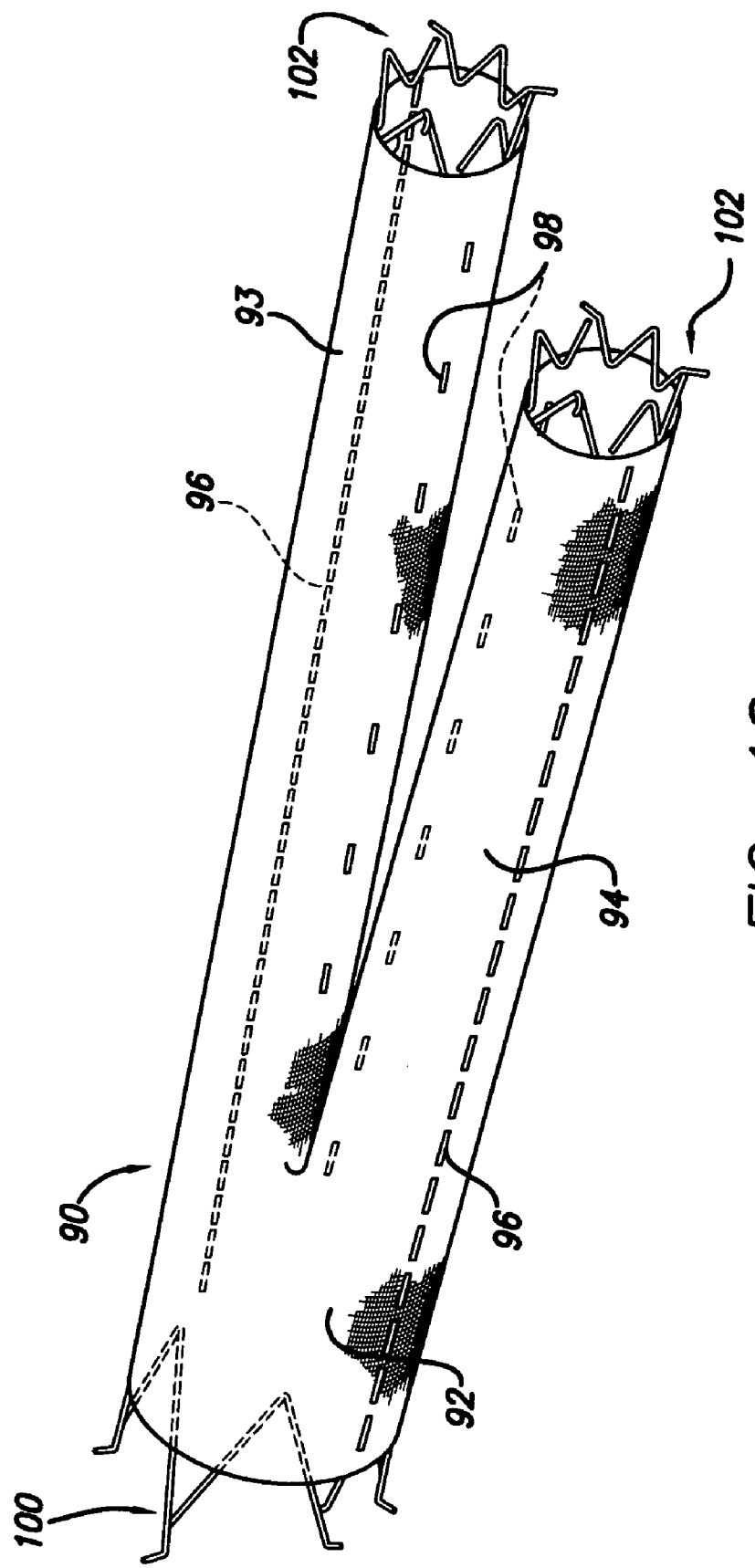
FIG. 18 depicts a perspective view of a graft assembly having a plurality of marker bands and attachment systems made in accordance with the present the invention.

Referring now to FIG. 18, the spray-formed materials of the present invention may be incorporated into a bifurcated graft 90. Likewise, the spray-formed materials may be incorporated into a tubular graft (not shown). Such a graft includes DACRON, PTFE or other suitable flexible material having an upper body 92, a first leg 93 and a second leg 94, wherein the legs are joined to the upper body. Such a configuration forms a "Y" or "pants leg" configuration. A plurality of closely spaced spray-formed or spray-coated markers 96 may be configured on the outside of the first and second legs. Similarly, wider spaced spray-formed or spray-coated markers 98 may be configured on the inside of the legs of the bifurcated graft (or visa versa). Such markers may be formed from a porous and/or drug impregnated material as heretofore described, and may be sewn, glued or otherwise bonded to the body and/or legs of the graft.

In many such grafts 90, such as those used for repairing an abdominal aortic aneurysm, the upper body may include a first attachment system 100 positioned proximate an upper (wider) opening of the graft. Tube grafts may contain a like attachment system at the lower openings of the graft. Similarly, bifurcated grafts may include smaller attachment systems 102 positioned at the end of the legs and proximate the lower (narrower) openings of the graft. Such attachment systems may be of various configurations, such as, but not limited to, a ring and link design, a zigzag design, a coil design, a slotted tube design or a tubular mesh design. As heretofore described regarding stents (FIGS. 11-15), the attachment system may be made from a variety of biocompatible materials and may be spray-formed or coated using a spray process. The attachment systems may be formed from a porous and/or drug impregnated material as heretofore described.

The illustrative stent 10 of the present invention and similar medical device structures can be made-in many ways. One method of making such a stent is to cut tube stock or sheets of substrate formed according to the method and devices of the present invention so as to remove portions of the tube stock in the desired pattern for the stent, leaving relatively untouched the portions of the tube stock that are to form, for example, the cylindrical rings 12 and links 13. Various processes of forming the desired stent pattern are available and are known in the art, such as, but not limited to, using laser or chemical etching, electronic discharge machining and stamping.

Figure 19:
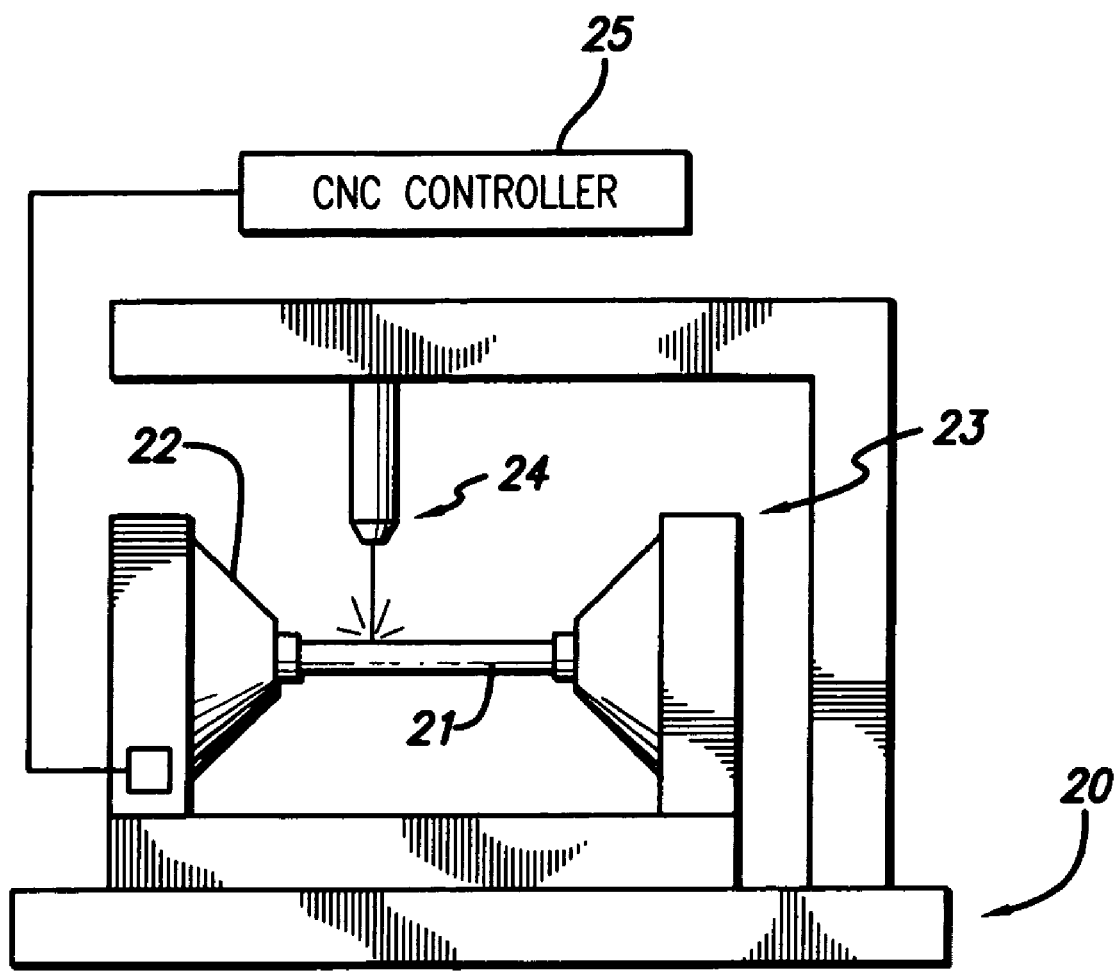
FIG. 19 depicts a schematic representation of equipment for laser cutting tube stock in the manufacture of a medical device made in accordance with the present invention.

A machine-controlled laser system 20 may be used to cut a desired pattern in a spray-formed or spray-coated tube stock 21, as illustrated schematically in FIG. 19 and as is known in the art. The tube stock may put in a rotatable collet fixture 22 of a machine-controlled apparatus 23 for positioning the tube stock relative to a laser 24. According to machine-encoded instructions, the tubing is rotated and moved longitudinally relative to the laser. The laser selectively removes material from the tube stock by ablation, and a desired pattern is cut into the tube stock as programmed in a computerized numeric controller (CNC) 25. After laser cutting, the near net-shaped stent 10 may be surface modified by a number of methods known in the art, including bead blasting, etching and electropolishing.

Cutting a fine structure, such as a stent 10, via a machine-controlled laser 20 requires minimal heat input and the ability to manipulate the tube stock 21 with precision. It is also necessary to support the tube stock, yet not allow the tube stock to distort during the cutting operation. To achieve a relatively small geometry of a desired stent pattern formed with ring struts 12 and links 13 sized for human vasculature, it is necessary to have very precise control of the laser's power level, focused spot size and positioning of the laser cutting path, which is well known in the art.

Referring now to FIG. 20, a stent 10 manufacture by a spray process in accordance with the present invention may be mounted onto a delivery catheter 11. The delivery catheter may also be constructed from spray-formed components, and typically has a distal expandable portion or balloon 14 for expanding the stent within an artery 15. Portions of the proximal end of such a catheter can be made of spray-formed metal tubing or metal wire. The balloon may be formed of suitable materials such as polyethylene, polyethylene terephthalate, polyvinyl chloride, nylon and ionomers such as SURLYN manufactured by the Polymer Products Division of the Du Pont Company. Other polymers may also be used. In order for the stent to remain in place on the balloon during delivery to the site of the damage within the artery, the stent is compressed onto the balloon.

The delivery of the stent 10 is accomplished in the following manner. The stent is first mounted onto the inflatable balloon 14 on the distal extremity of the delivery catheter 11. The catheter-stent assembly is introduced within the patient's vasculature in a conventional Seldinger technique through a guiding catheter (not shown). A guidewire 18 is disposed across the damaged arterial section, and then the catheter/stent assembly is advanced over the guidewire within the artery until the stent is directly within the target site. As stated, the manufacture of guidewires also will benefit from the spray processes of the present invention. While the drawing figures illustrate a rapid exchange (Rx) intravascular catheter and guidewire, medical devices of the present invention may be also used with an over-the-wire (OTW) intravascular catheter. Additionally, although a balloon expandable stent and associate catheter assembly are depicted, a self-expanding stent in combination with an appropriate alternative catheter assembly may be used.

Once the stent 10 is positioned at the desired location, the balloon 14 of the catheter 11 is expanded, forcing the stent against the wall of the artery 15, as illustrated in FIG. 21. While not shown in the drawing, the artery may be expanded slightly by the expansion of the stent to seat or otherwise fix the stent to prevent movement. In some circumstances, during the treatment of stenotic portions of an artery, the lumen of the artery may have to be expanded considerably in order to facilitate passage of blood or other fluid through the vessel lumen.

The stent 10 serves to hold open the artery 15 after the balloon 14 is deflated and the catheter 11 is withdrawn, as illustrated by FIG. 22. Due to the formation of the stent from an elongated tubular member, the undulating component of the rings 12 of the stent is relatively flat in transverse cross-section, so that when the stent is expanded, the rings are pressed into the wall of the artery and, as a result, do not interfere with the blood flow through the artery. Furthermore, the closely spaced rings and links 13 provide uniform support for the wall of the artery and, consequently, are well adapted to hold open the artery. A porous stent containing one or more of the drugs and therapeutic agents disclosed herein may be used to reduce thrombosis and/or restenosis of the target vessel.

While several particular forms of the invention have been illustrated and described, it will also be apparent that various modifications can be made without departing from the scope of the invention.

What is claimed:

1. A method of manufacturing a medical device, comprising:
   providing a biocompatible material;
   using a spray process to form a porous substrate from the biocompatible material; and
   processing the porous substrate into a medical device.

2. The method of claim 1, further comprising applying a therapeutic agent to the porous substrate.

3. The method of claim 2, wherein applying the therapeutic agent to the porous substrate includes selecting the therapeutic agent from the group consisting of antiplatelets, anticoagulants, antifibrins, antiinflammatories, antithrombins, and antiproliferatives.

4. The method of claim 2, wherein applying the therapeutic agent to the porous substrate includes impregnating the porous substrate with paclitaxel.

5. The method of claim 1, wherein providing the biocompatible material includes providing a metal alloy selected from the group consisting of iron-based, cobalt-based and titanium-based alloys.

6. The method of claim 1, wherein processing the porous substrate includes forming a stent.

7. The method of claim 6, further comprising applying a polymer layer on an outer surface of the stent.

8. The method of claim 6, further comprising using a spray process to form a porous layer of the biocompatible materials on an outer surface of the stent.

9. A method of manufacturing a drug eluting stent, comprising:
providing a biocompatible material;
forming a porous substrate from the biocompatible material, wherein a spray process is used;
processing the porous substrate into a porous tube stock; and
forming a pattern in the porous tube stock to form a porous stent.

10. The method of claim 9, further comprising applying a therapeutic agent to the porous substrate.

11. The method of claim 10, wherein applying the therapeutic agent to the porous substrate includes selecting the therapeutic agent from the group consisting of antiplatelets, anticoagulants, antifibrins, antiinflammatories, antithrombins, and antiproliferatives.

12. The method of claim 10, wherein applying the therapeutic agent to the porous substrate includes impregnating the porous substrate with paclitaxel.

13. The method of claim 9, wherein providing the biocompatible material includes providing a metal alloy selected from the group consisting of iron-based, cobalt-based and titanium-based alloys.

14. The method of claim 9, further comprising applying a polymer layer on an outer surface of the stent.

15. The method of claim 9, further comprising using a spray process to form a porous layer of the biocompatible material on an outer surface of the stent.

16. A method of coating a medical device, comprising:
providing a medical device;
providing a coating material;
applying the coating material to the medical device by cold spray thermal processing wherein powder particles are introduced into a high pressure gas where both the gas and particles enter a supersonic jet which is directed against the medical device forming a porous coating, and wherein the medical device is selected from the group consisting of a stent, guide wires, lead tips, catheters, and markers;
wherein the porous coating is functionally graded,
wherein the thickness of the coating on the medical device is varied, and
applying a drug to the porous coating on the medical device.

17. The method of claim 16, wherein applying the drug to the porous coating includes selecting the drug from the group consisting of antiplatelets, anticoagulants, antifibrins, antiinflammatories, antithrombins, and antiproliferatives.

18. The method of claim 16, wherein providing the coating material includes providing a metal alloy selected from the group consisting of iron-based, cobalt-based and titanium-based alloys.

19. The method of claim 16, wherein providing the medical device includes forming a stent.

20. A method of manufacturing a medical device, comprising:
providing a biocompatible material; and
using a spray process to form a porous substrate from the biocompatible material on a medical device, such that the formed porous substrate exhibits a functionally graded coating over at least a portion of the medical device;
wherein the using a spray process to form a porous substrate step is such that the formed porous substrate includes a first porous layer having a first density and a second porous layer having a second density greater than the first density.

21. A method of manufacturing a medical device, comprising:
providing a biocompatible material; and
using a spray process to form a porous substrate from the biocompatible material on a medical device, such that the formed porous substrate exhibits a functionally graded coating over at least a portion of the medical device;
wherein the using a spray process to form a porous substrate step is such that different degrees of density and porosity are formed over at least a portion of the medical device.

22. A method of manufacturing a medical device, comprising:
providing a biocompatible material; and
using a spray process to form a porous substrate from the biocompatible material on a medical device, such that the formed porous substrate exhibits a functionally graded coating over at least a portion of the medical device;
further including the step of impregnating the porous substrate with a drug or therapeutic agent.

23. A method of manufacturing a medical device, comprising:
providing a biocompatible material; and
using a spray process to form a porous substrate from the biocompatible material on a medical device, such that the formed porous substrate exhibits a functionally graded coating over at least a portion of the medical device;
further including the step of varying the thickness of the porous substrate.

24. A method of manufacturing a medical device, comprising:
providing a biocompatible material;
using a spray process to form a porous substrate from the biocompatible material on a base material, such that the formed porous substrate exhibits a functionally graded coating over at least a portion of the medical device; and
processing the porous substrate into a medical device.

* * * * *